United States Patent
Lee et al.

(10) Patent No.: US 12,357,718 B2
(45) Date of Patent: Jul. 15, 2025

(54) IMAGE PROCESSING DEVICE AND IMAGE PROCESSING METHOD

(71) Applicant: MEDIT CORP., Seoul (KR)

(72) Inventors: Dong Hoon Lee, Seoul (KR); Jae Min You, Seoul (KR)

(73) Assignee: MEDIT CORP., Seoul (KR)

( * ) Notice: Subject to any disclaimer, the term of this patent is extended or adjusted under 35 U.S.C. 154(b) by 112 days.

(21) Appl. No.: 18/025,983

(22) PCT Filed: Sep. 16, 2021

(86) PCT No.: PCT/KR2021/012719
§ 371 (c)(1),
(2) Date: Mar. 13, 2023

(87) PCT Pub. No.: WO2022/060133
PCT Pub. Date: Mar. 24, 2022

(65) Prior Publication Data
US 2023/0355819 A1 Nov. 9, 2023

(30) Foreign Application Priority Data

Sep. 17, 2020 (KR) .................. 10-2020-0119770
Sep. 15, 2021 (KR) .................. 10-2021-0123166

(51) Int. Cl.
*A61L 2/24* (2006.01)
*A61L 2/10* (2006.01)
(Continued)

(52) U.S. Cl.
CPC .................. *A61L 2/24* (2013.01); *A61L 2/10* (2013.01); *A61L 2/28* (2013.01); *H04N 13/207* (2018.05);
(Continued)

(58) Field of Classification Search
CPC ..... A61L 2/24; A61L 2/10; A61L 2/28; A61L 2202/11; A61L 2202/14; A61L 2202/16;
(Continued)

(56) References Cited

U.S. PATENT DOCUMENTS

2015/0071819 A1 3/2015 Todeschini
2015/0216294 A1 8/2015 Mongan et al.
(Continued)

FOREIGN PATENT DOCUMENTS

EP           3 616 599 A1    3/2020
KR    10-2003-0093754 A     12/2003
(Continued)

OTHER PUBLICATIONS

International Search Report for PCT/KR2021/012719 dated Dec. 23, 2021.
(Continued)

*Primary Examiner* — Joseph W Becker
(74) *Attorney, Agent, or Firm* — Sughrue Mion, PLLC

(57) ABSTRACT

Provided is a handheld scanner. The handheld scanner includes one or more UVC LED elements and a processor configured to execute one or more instructions, wherein the processor is configured to, by executing the one or more instructions, control the one or more UVC LED elements to be turned on in response to detecting a first event, and control the one or more UVC LED elements to be turned off in response to detecting a second event while the one or more UVC LED elements are turned on to operate.

17 Claims, 11 Drawing Sheets

(51) Int. Cl.
    *A61L 2/28*      (2006.01)
    *H04N 13/207*    (2018.01)
    *H04N 23/56*     (2023.01)
    *H04N 23/62*     (2023.01)
    *H04N 23/74*     (2023.01)

(52) U.S. Cl.
    CPC ............. *H04N 23/56* (2023.01); *H04N 23/62* (2023.01); *H04N 23/74* (2023.01); *A61L 2202/11* (2013.01); *A61L 2202/14* (2013.01); *A61L 2202/16* (2013.01)

(58) Field of Classification Search
    CPC ...... H04N 13/207; H04N 23/56; H04N 23/62; H04N 23/74; H04N 1/00909; H04N 1/107; H04N 1/1071; A61C 9/0046; A61C 9/0053
    See application file for complete search history.

(56) References Cited

U.S. PATENT DOCUMENTS

| | | |
|---|---|---|
| 2015/0313354 A1 | 11/2015 | Mongan et al. |
| 2017/0000916 A1 | 1/2017 | Stibich et al. |
| 2020/0069169 A1* | 3/2020 | Tanaka ............... A61B 1/00194 |
| 2020/0170497 A1 | 6/2020 | Chang et al. |
| 2022/0331469 A1* | 10/2022 | Liu ........................... A61L 2/10 |

FOREIGN PATENT DOCUMENTS

| | | |
|---|---|---|
| KR | 10-1767940 B1 | 8/2017 |
| KR | 10-2018-0023000 A | 3/2018 |
| KR | 10-2020-0064922 A | 6/2020 |

OTHER PUBLICATIONS

Extended European Search Report dated Jul. 4, 2024 in Application No. 21869755.5.

* cited by examiner

IMAGE PROCESSING DEVICE AND IMAGE PROCESSING METHOD

CROSS REFERENCE TO RELATED APPLICATIONS

This application is a National Stage of International Application No. PCT/KR2021/012719 filed Sep. 16, 2021, claiming priority based on Korean Patent Application No. 10-2020-0119770 filed Sep. 17, 2020 and Korean Patent Application No. 10-2021-0123166 filed Sep. 15, 2021.

TECHNICAL FIELD

Various embodiments disclosed herein relate to an image processing device and an image processing method, and more particularly, to an image processing device and an image processing method, to sterilize the interior of a handheld scanner.

BACKGROUND ART

Handheld scanners include a tip that is inserted into an object to be scanned and a scanner main body. The tip that is inserted into the object can be separated and sterilized in a sterilizer. However, the use of a sterilizer for the scanner main body is impossible because the scanner main body has a structure that is difficult for users to separate, and there is a possibility of damage to inner components. A sterilization operation may be performed only on the exterior of the scanner main body by using an alcohol cleaning solution, and it is difficult to perform a sterilization operation on the interior thereof. Therefore, there is a limit to hygienically using the scanner main body.

DISCLOSURE

Technical Solution

A handheld scanner according to an embodiment may include one or more UVC LED elements and a processor configured to execute one or more instructions, wherein the processor is configured to, by executing the one or more instructions, control the one or more UVC LED elements to be turned on in response to detecting a first event, and control the one or more UVC LED elements to be turned off in response to detecting a second event while the one or more UVC LED elements are turned on to operate.

MODE FOR INVENTION

Figure 1:
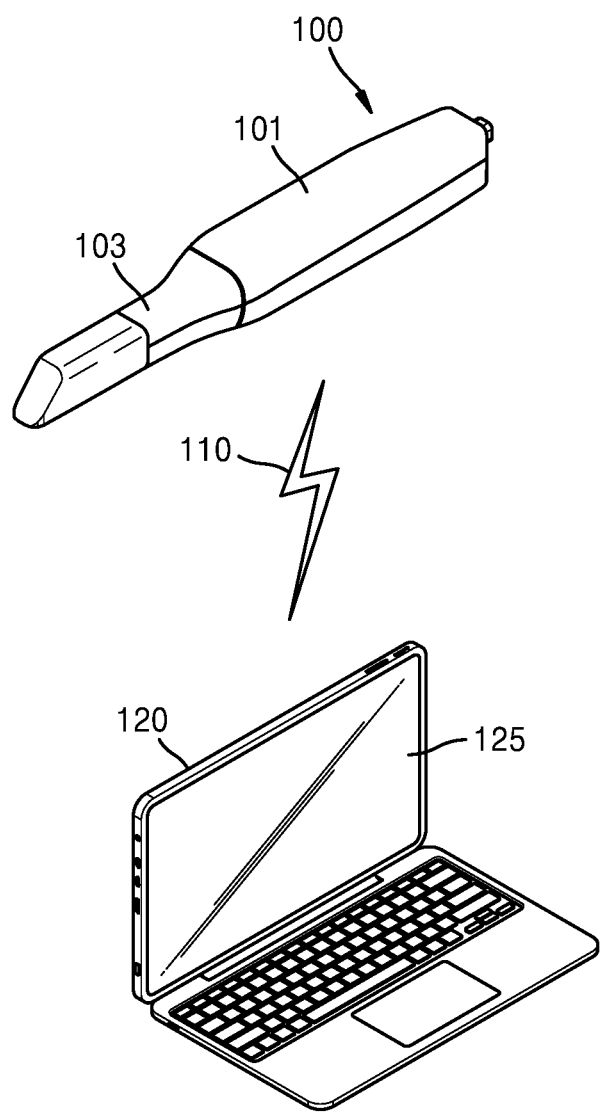
FIG. 1 is a view for explaining an image processing system according to an embodiment.

In an embodiment, the handheld scanner may further include a user input unit and a communicator configured to transmit/receive information to/from a data processing device, wherein the first event may include at least one of receiving a first control signal through the user input unit, and receiving a first control signal from the data processing device through the communicator, and the first control signal may include at least one of a scan mode off command, a power on command for the handheld scanner, and a power on command for the one or more UVC LED elements.

In an embodiment, the first event may include at least one of ending of calibration of the handheld scanner, entering a standby mode, which is performed by the handheld scanner, and elapsing of a preset time after the handheld scanner enters the standby mode.

In an embodiment, the handheld scanner may further include a projector including a light source, wherein the processor may be further configured to, by executing the one or more instructions, prevent the light source included in the projector and the one or more UVC LED elements from operating at the same time.

In an embodiment, the handheld scanner may further include a camera configured to obtain two-dimensional image data about an object, wherein the processor may be further configured to, by executing the one or more instructions, prevent the camera from obtaining the two-dimensional image data while the one or more UVC LED elements are turned on to operate, or prevent the two-dimensional image data, obtained by the camera while the one or more UVC LED elements are turned on to operate, from being used when a three-dimensional image is generated.

In an embodiment, the handheld scanner may further include a user input unit and a communicator configured to transmit/receive information to/from a data processing device, wherein the second event may include at least one of receiving a second control signal through the user input unit, and receiving a second control signal from the data processing device through the communicator, and the second control signal may include at least one of a scan mode entry command, a power off command for the handheld scanner, and a power off command for the one or more UVC LED elements.

In an embodiment, the second event may include an elapse of a preset time after the one or more UVC LED elements are turned on to irradiate UVC.

In an embodiment, the processor may be further configured to, by executing one or more instructions, when the one or more UVC LED elements are turned on to operate, perform a scan operation by omitting preheating of the handheld scanner, or perform a scan operation after preheating the handheld scanner for a time shorter than a preset preheating time.

In an embodiment, the handheld scanner may further include a fan configured to introduce outside air, wherein the one or more UVC LED elements may be arranged in a path where a flow rate of the outside air introduced by the fan is greater than or equal to a reference value.

In an embodiment, the handheld scanner may further include an optical module, wherein the one or more UVC LED elements may be arranged in the optical module.

In an embodiment, the handheld scanner may include a handheld scanner main body and a tip coupled to the handheld scanner main body in a detachable manner, wherein the one or more UVC LED elements may be arranged near a portion of the handheld scanner main body, which is coupled to the tip.

A data processing device according to an embodiment includes a communicator configured to transmit/receive information to/from a handheld scanner including one or more UVC LED elements, a memory storing one or more instructions, and a processor configured to execute the one or more instructions stored in the memory, wherein the processor may be configured to, by executing the one or more instructions, control the one or more UVC LED elements included in the handheld scanner to be turned on by transmitting a first control signal to the handheld scanner through the communicator, or control the one or more UVC LED elements to be turned off by transmitting a second control signal to the handheld scanner through the communicator while the one or more UVC LED elements are turned on to operate.

In an embodiment, the first control signal may include at least one of a scan mode off command, a power on command for the handheld scanner, and a power on command for the one or more UVC LED elements, and the second control signal may include at least one of a scan mode entry command, a power off command for the handheld scanner, and a power off command for the one or more UVC LED elements.

In an embodiment, the data processing device may further include a user input unit of the data processing device, and a display, wherein a user interface screen for receiving a selection of whether to perform UVC LED element auto-on may be output through the display, a selection of the UVC LED element auto-on may be received through the user input unit of the data processing device in response to the user interface screen, and the processor may be further configured to, by executing the one or more instructions, in response to receiving the selection of the UVC LED element auto-on, control the one or more UVC LED elements mounted in the handheld scanner to be powered on by transmitting the first control signal to the handheld scanner through the communicator, or control the one or more UVC LED elements to be powered off by transmitting the second control signal to the handheld scanner through the communicator.

An image processing method performed by an image processing device, according to an embodiment, may include controlling one or more UVC LED elements included in a handheld scanner to be turned on in response to detecting a first event, and controlling the one or more UVC LED elements to be turned off in response to detecting a second event while the one or more UVC LED elements are turned on to operate.

The present specification describes the principle of the disclosure and discloses embodiments to clarify the scope of rights of the disclosure and enable one skilled in the art to which the disclosure pertains to work the disclosure. The disclosed embodiments may be implemented in various forms.

Throughout the specification, like reference numerals denote like constituent elements. The present specification does not describe all elements of embodiments, and general matters in the technical field to which the disclosure pertains, or redundant descriptions between embodiments, are omitted. Terms such as "part" or "portion" used in the specification may be embodied by software or hardware, and according to embodiments, a plurality of "parts" or "portions" may be embodied as one unit or elements or one "part" or "portion" may include a plurality of units or elements. Hereinafter, the operation principle and embodiments of the disclosure are described with reference to the accompanying drawings.

In the present specification, an object is a subject to be photographed and may include a part of a body or a model of the part of the body. For example, an object may include various body parts, such as an ear, nose, oral cavity of a human or animal, or models thereof.

In the present specification, an image may include an image that represents an object. In the present specification, an image may include an image (hereinafter, referred to as the "intraoral image") representing at least one tooth, an oral cavity including at least one tooth, or an oral cavity plaster model.

In addition, in the present specification, an intraoral image may be a two-dimensional image of an object or a three-dimensional intraoral image that represents an object in three-dimensions. As a three-dimensional intraoral image may be generated by three-dimensionally modeling a structure of an oral cavity, based on raw data, the three-dimensional intraoral image may be referred to as a three-dimensional oral cavity model. In addition, a three-dimensional oral cavity model may be referred to as a three-dimensional scan model or three-dimensional scan data. Hereinafter, in the present specification, an intraoral image is used to collectively mean a model or image two-dimensionally or three-dimensionally representing an oral cavity.

However, in the present specification, an image is not limited to an intraoral image, and may include an image of various objects, such as an ear or a nose, according to the type and body part of an object.

In addition, in the present specification, data may mean information needed to express an object in two-dimensions or three-dimensions, for example, raw data obtained by using at least one camera.

In detail, raw data is data obtained to generate an image, that is, data (for example, two-dimensional data) obtained from at least one image sensor included in a three-dimensional scanner when an object is scanned by using a three-dimensional scanner. Raw data obtained from a three-dimensional scanner may be referred to as two-dimensional image data. Raw data may mean two-dimensional images of different viewpoints obtained by a plurality of cameras when an object is scanned by using a three-dimensional scanner.

In the above, it has been described that raw data is a two-dimensional image, but is not limited thereto, and raw data may be three-dimensional image data.

A handheld scanner may be a hygiene-sensitive device because the handheld scanner may be inserted into an oral cavity, an ear, a nose, or the like. In particular, unlike a tip, a main body of a handheld scanner cannot be used in a sterilizer due to the possibility of damage to inner components.

Disclosed embodiments are to overcome the above problems, and provided are an image processing device and an image processing method, to sterilize the interior of a handheld scanner by arranging a UVC LED element in the handheld scanner.

Hereinafter, embodiments are described in detail with reference to the accompanying drawings.

FIG. 1 is a view for explaining an image processing system according to an embodiment.

Referring to FIG. 1, an image processing system may include a handheld scanner 100 and a data processing device 120 coupled to the handheld scanner 100 through a communication network 110.

The handheld scanner 100 may be a medical device for obtaining an image of an object.

The handheld scanner 100 may obtain an image of at least one of an oral cavity, an ear, a nose, an artificial structure, and a plaster model of the oral cavity, the ear, the nose, or the artificial structure.

In an embodiment, the handheld scanner 100 may be of a handheld type that allows a user to scan an object while holding the handheld scanner 100 in a hand and moving. The handheld scanner 100 may obtain an image of the inside of an ear or nose by being inserted into the ear or nose to scan the inside of the ear or nose in a non-contact manner.

Alternatively, the handheld scanner 100 may be an intraoral scanner that obtains an intraoral image of an oral cavity including at least one tooth by being inserted into the oral cavity to scan a tooth. Hereinafter, for convenience of description, a case where the handheld scanner 100 is an intraoral scanner is described as an example, but the disclosure is not limited thereto.

The handheld scanner 100 may include a main body 101 and a tip 103. The main body 101 may include a light projector (not shown) that projects light and a camera (not shown) that captures and obtains an image of an object.

The tip 103 is inserted into an oral cavity and may be mounted on the main body 101 in a detachable manner. The tip 103 includes a light path changing unit to direct light projected from the main body 101 to an object and direct light received from the object to the main body 101.

The handheld scanner 100 may obtain surface information about an object, as raw data, for imaging of at least one surface of a tooth inside an oral cavity, a gingiva, and an artificial structure (for example, an orthodontic appliance including a bracket, a wire, and the like, an implant, an artificial tooth, an orthodontic auxiliary inserted in an oral cavity, and the like) that is insertable in an oral cavity.

The handheld scanner 100 may transmit the obtained raw data to the data processing device 120 through the communication network 110.

In an embodiment, the handheld scanner 100 may include one or more UVC LED elements (not shown) therein.

In an embodiment, the handheld scanner 100 may include a fan for introducing outside air, and one or more UVC LED elements may be arranged in a path where a flow rate of outside air introduced by the fan is greater than or equal to a reference value.

In an embodiment, the handheld scanner 100 may include an optical module including a camera, and one or more UVC LED elements may be arranged near the optical module or in the optical module.

In an embodiment, a UVC LED element may be arranged near a portion of the main body 101 of the handheld scanner 100, which is coupled to the tip 103.

In an embodiment, the handheld scanner 100 may control one or more UVC LED elements to be turned on in response to detecting a first event.

In an embodiment, the first event may include receiving a first control signal through a user input unit included in the main body 101 of the handheld scanner 100 or receiving a first control signal from the data processing device 120 through the communication network 110. The first control signal may include at least one of a power on command for the main body 101 of the handheld scanner 100 or a power on command for one or more UVC LED elements included in the handheld scanner 100.

In an embodiment, the first event may include ending of the calibration of the handheld scanner 100. The handheld scanner 100 may control one or more UVC LED elements to be turned on in response to the completion of the calibration.

In an embodiment, the first event may include entering the handheld scanner 100 into a standby mode. The handheld scanner 100 may control one or more UVC LED elements to be turned on in response to the handheld scanner 100 entering the standby mode.

In an embodiment, the first event may include elapsing of a preset time after the handheld scanner 100 enters the standby mode. The handheld scanner 100 may control one or more UVC LED elements to be turned on when the preset time elapses after the handheld scanner 100 enters the standby mode.

In an embodiment, the handheld scanner 100 may include a projector including a light source, and one or more UVC LED elements may be arranged in the projector.

When the handheld scanner 100 operates in a scan mode, the handheld scanner 100 may allow the light source included in the projector to project light and allow the camera included in the optical module to obtain a two-dimensional image of an object. When a UVC LED element operates while the handheld scanner 100 scans an object, precise three-dimensional scan data may not be obtained due to UVC projected by the UVC LED element.

Therefore, in an embodiment, the handheld scanner 100 may prevent one or more UVC LED elements from operating while the handheld scanner 100 scans an object.

In an embodiment, the handheld scanner 100 may control one or more UVC LED elements not to be turned on simultaneously while an RGB light source included in the projector is turned on and emits light.

In an embodiment, the handheld scanner 100 may control the camera not to obtain a two-dimensional image of an object while one or more UVC LED elements operate. Alternatively, the handheld scanner 100 may prevent a two-dimensional image of an object, which is obtained by the camera while one or more UVC LED elements operate, from being used when a three-dimensional oral cavity model is generated.

In an embodiment, when detecting a second event while one or more UVC LED elements are turned on, the handheld scanner 100 may control the one or more UVC LED elements to be turned off in response to the detection of the second event.

In an embodiment, the second event may include receiving a second control signal through the user input unit included in the main body 101 of the handheld scanner 100 or receiving a second control signal from the data processing device 120 through the communication network 110. The second control signal may include at least one of a scan mode entry command, a power off command for the handheld scanner 100, and a power off command for one or more UVC LED elements.

In an embodiment, the second event may include one or more UVC LED elements being turned on to irradiate UVC and elapsing of a preset time. The handheld scanner 100 may control a UVC LED element to be automatically turned off when the preset time elapses after the UVC LED element operates.

The data processing device 120 may be connected to the handheld scanner 100 through the wired or wireless communication network 110. The data processing device 120 may be any electronic device capable of receiving raw data from the handheld scanner 100, and generating, processing, displaying, and/or transmitting an intraoral image, based on the received raw data. For example, the data processing device 120 may be a computing device, such as a smart phone, a laptop computer, a desktop computer, a personal digital assistant (PDA), or a tablet personal computer (PC), but is not limited thereto. In addition, the data processing device 120 may exist in the form of a server (or a server device) for processing an intraoral image.

In an embodiment, the data processing device 120 may transmit a control signal to the handheld scanner 100 to control the operation of the handheld scanner 100. In an embodiment, the control signal transmitted to the handheld scanner 100 by the data processing device 120 may include at least one of a power on/off command for the handheld scanner 100 and a power on/off command for one or more UVC LED elements included in the handheld scanner 100.

The data processing device 120 may process two-dimensional image data to generate a three-dimensional intraoral image or generate additional information, based on the two-dimensional image data received from the handheld scanner 100. The data processing device 120 may display the three-dimensional intraoral image and/or the additional information through a display 125, or may output or transmit the three-dimensional intraoral image and/or the additional information to an external device.

As another example, the handheld scanner 100 may obtain raw data through the oral cavity scanning, generate three-dimensional data by processing the obtained raw data, and transmit the three-dimensional data to the data processing device 120.

The handheld scanner 100 may project patterned light onto an object and scan the object onto which the patterned light is projected, to obtain three-dimensional data representing the shape of the object by using the principle of triangulation by pattern deformation.

In an embodiment, the handheld scanner 100 may obtain three-dimensional data about an object by using a confocal method. The confocal method is a non-destructive optical imaging technique for three-dimensional surface measurement, and an optically sectioned image with a high spatial resolution may be obtained by using a pinhole structure. The handheld scanner 100 may obtain three-dimensional data by stacking two-dimensional images obtained in an axial direction.

However, this is merely exemplary, and the handheld scanner 100 may obtain three-dimensional data from raw data by using various methods other than the above-described method, and may transmit the three-dimensional data to the data processing device 120. The data processing device 120 may analyze, process, display, and/or transmit the received three-dimensional data.

Figure 2:
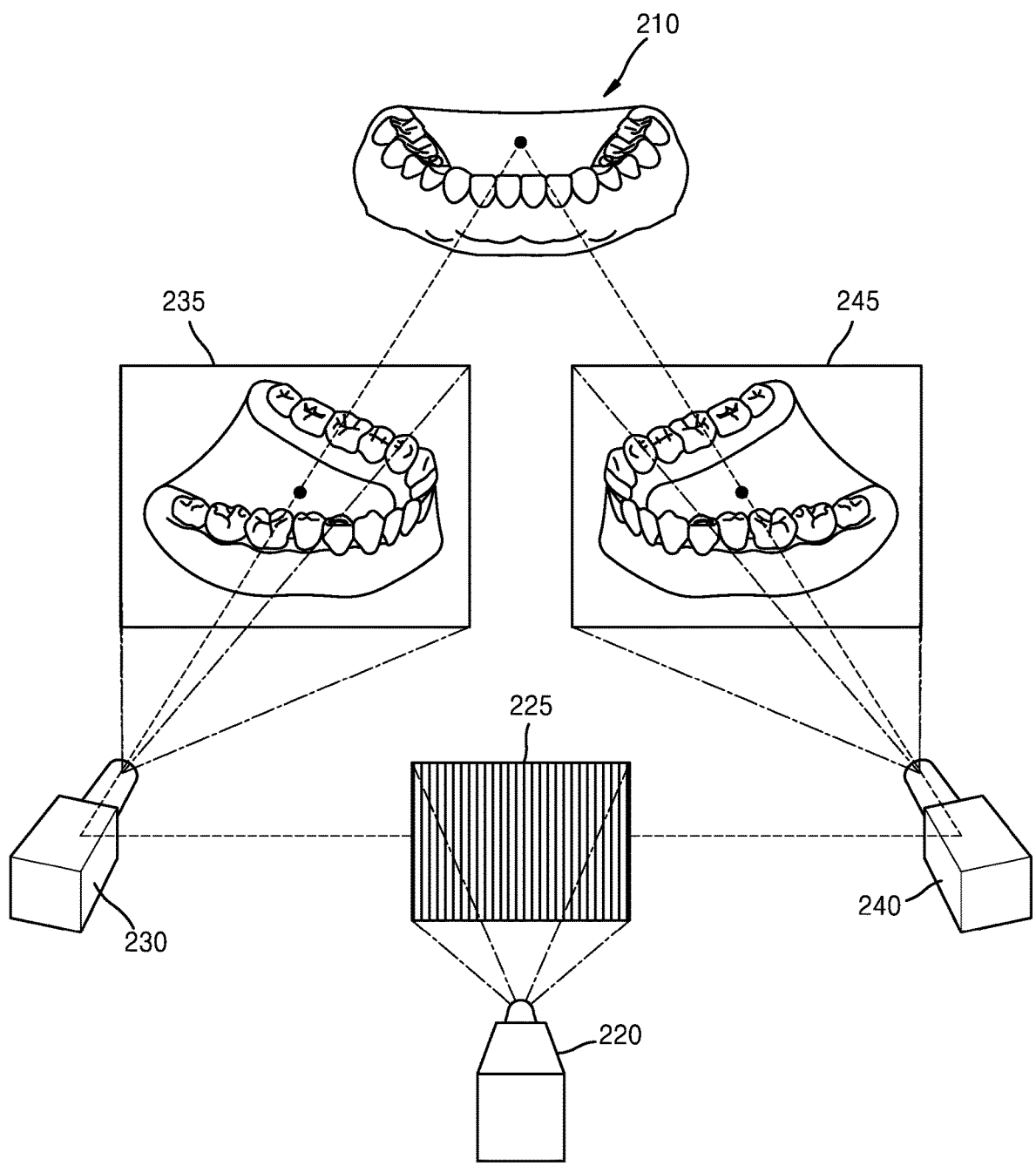
FIG. 2 is a view for explaining a method, performed by a handheld scanner, of obtaining surface data, according to an embodiment.

FIG. 2 is a view for explaining a method, performed by a handheld scanner, of obtaining surface data, according to an embodiment.

In an embodiment, the handheld scanner 100 may obtain three-dimensional data about an object by using various methods. For example, the handheld scanner 100 may obtain three-dimensional data about an object by using a confocal method. The confocal method is a method of obtaining three-dimensional information of an object, based on the position of a point found by using a maximum intensity of light reflected according to a refractive index of a lens that passes light projected onto the object. The handheld scanner 100 may obtain an optically sectioned image with a high spatial resolution by using a pinhole structure. The handheld scanner 100 may obtain three-dimensional data by stacking two-dimensional images obtained in an axial direction.

Alternatively, in another embodiment, the handheld scanner 100 may obtain three-dimensional image of an object by using a triangulation technique. The triangulation technique is a technique for obtaining three-dimensional information of an object through triangulation by using a triangle formed by a light source, an object onto which light projected from the light source is projected, and an image sensor to which the light reflected from the object is input. However, this is merely exemplary, and the handheld scanner 100 may obtain three-dimensional data by using various methods other than the confocal method or the triangulation technique.

Hereinafter, as an embodiment, a method, performed by the handheld scanner 100, of obtaining three-dimensional data about an image by using a triangulation technique is described in detail.

In an embodiment, the handheld scanner 100 may obtain an image by using at least one camera, and may obtain three-dimensional data based on the obtained image.

In FIG. 2, the handheld scanner 100 may be an optical three-dimensional scanner. The handheld scanner 100 may use a structured light with a stereo version method to obtain three-dimensional data about a surface of an object 210.

The handheld scanner 100 may include two or more cameras including an L camera 230 and an R camera 240 and a projector 220 capable of projecting structured light 225.

The handheld scanner 100 may project the structured light 225 onto the object 210, and may obtain an L image 235 corresponding to a left field of view and an R image 245 corresponding to a right field of view from the L camera 230 corresponding to the left field of view and the R camera 240 corresponding to the right field of view, respectively. The L image 235 and the R image 245 may be reconstructed into three-dimensional image frames representing the surface of the object 210.

The handheld scanner 100 may continuously obtain two-dimensional image frames including the L image 235 and R image 245 of the object 210. The handheld scanner 100 or the data processing device 120 may obtain three-dimensional image frames representing the shape of the surface of the object 210 from the two-dimensional image frames including the L image 235 and the R image 245. In FIG. 2, the handheld scanner 100 obtains three-dimensional data from two images obtained by using the two cameras 230 and 240, but this is merely exemplary, and the handheld scanner 100 may obtain an image by using one of the two cameras 230 and 240.

The handheld scanner 100 may obtain a plurality of two-dimensional frames by scanning the periphery of the object 210 at regular time intervals (for example, 10 to 30 frames per second). The handheld scanner 100 or the data processing device 120 may obtain a plurality of three-dimensional image frames from the plurality of two-dimensional image frames.

The data processing device 120 may obtain a three-dimensional oral cavity model of the object 210 as a whole by merging or aligning the plurality of three-dimensional image frames.

Figure 3:
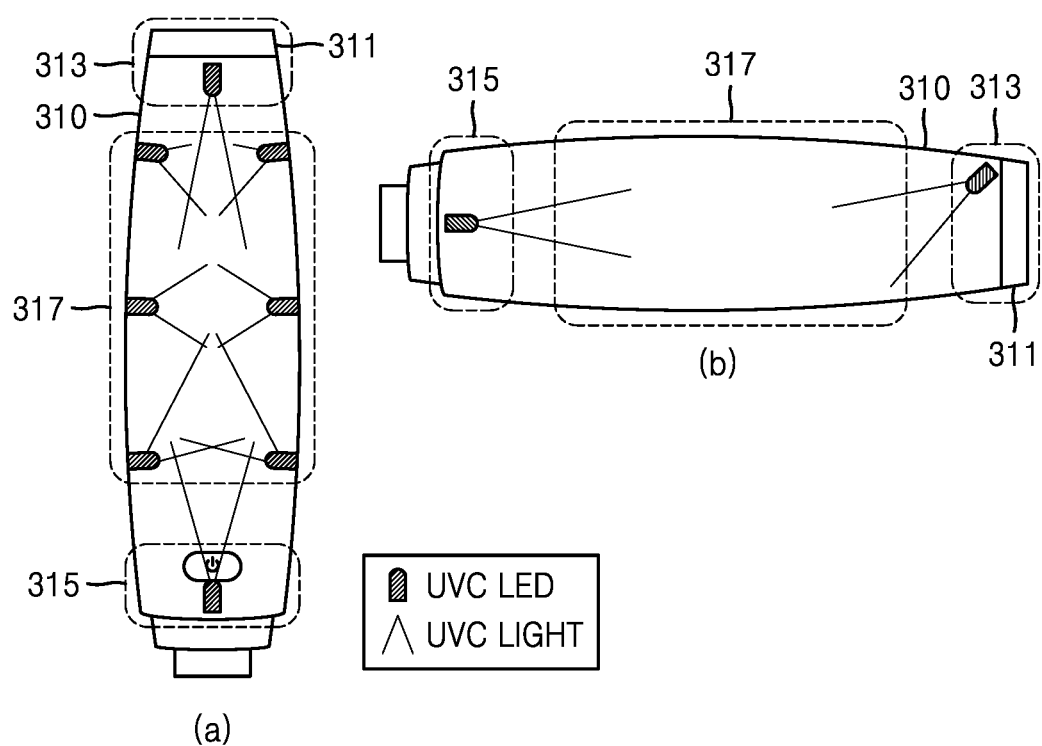
FIG. 3 is a view for explaining that one or more UVC LED elements are arranged in a handheld scanner, according to an embodiment.

FIG. 3 is a view for explaining that one or more UVC LED elements are arranged in a handheld scanner, according to an embodiment.

Referring to FIG. 3, one or more UVC LED elements may be arranged in a handheld scanner main body 310.

Ultraviolet light is a region of invisible wavelengths. Ultraviolet light is classified into UVA (long wavelength), UVB (medium wavelength), and UVC (short wavelength) depending on a wavelength. Among them, UVC may effectively remove bacteria, viruses, and other microorganisms by using light having a wavelength range from about 100 nm to about 280 nm. UVC may destroy the molecular structure of DNA or RNA of organism cells, causing DNA strand breakage and the breakage of nucleic acids and proteins, thus causing the death of bacteria and the death of regenerative cells.

In an embodiment, the handheld scanner may include a UVC LED element. The UVC LED element may be an LED element that irradiates UVC. The UVC LED element is a small LED light source, and for example, may be of a point light source type. The UVC LED element may be efficiently mounted on a small device, such as a handheld scanner.

Since UVC has an invisible wavelength of ultraviolet light, in an embodiment, an LED having a color, for example, a blue LED, may be additionally mounted on the handheld scanner main body 310 for safety. The handheld scanner main body 310 may indicate that the UVC LED element is in operation by using the additionally mounted blue LED. In other words, the handheld scanner main body 310 may allow the blue LED to be turned on to project blue light while the UVC LED element is turned on to irradiate UVC, and may allow the blue LED to be turned off when the UVC LED element is turned off and does not irradiate UVC.

(a) of FIG. 3 illustrates that eight UVC LED elements are mounted on the handheld scanner main body 310. However, this is merely exemplary, and various numbers of UVC LED elements may be arranged in various positions in the handheld scanner main body 310.

In an embodiment, the handheld scanner main body 310 may include a coupling portion 311 onto which a tip is mounted. In an embodiment, a UVC LED element may be mounted at a position 313 adjacent to the coupling portion 311 onto which the tip is mounted, and may sterilize air that may flow into the tip from the handheld scanner main body 310.

In an embodiment, the handheld scanner main body 310 may include a fan (not shown) positioned in a direction opposite to where the tip is mounted. The fan mounted on the handheld scanner main body 310 may cool the handheld scanner main body 310 by drawing in outside air, thereby removing heat generated from the handheld scanner main body 310. In an embodiment, a UVC LED element may be arranged at a position 315 near the fan to sterilize air introduced by the fan. The air introduced by the fan may move in the handheld scanner main body 310 in a state of being sterilized by the UVC LED element, and then may be exhausted to the outside of the handheld scanner main body 310.

In an embodiment, a UVC LED element may be mounted on a frame (or a case) 317 surrounding the handheld scanner main body 310, or may be mounted on constituent elements included in the handheld scanner main body 310, to irradiate UVC onto the constituent elements inside the handheld scanner main body 310. The irradiated UVC may sterilize a surface of the frame 317 or surfaces of the constituent elements inside the handheld scanner main body 310.

UVC projected by the UVC LED element may be reflected by the constituent elements included in the handheld scanner main body 310 or the inside of the frame 317. UVC may sterilize the constituent elements, an inner surface of the frame 317, and/or air while being reflected by the inside of the handheld scanner main body 310 and the inside of the frame 317 and thus moving.

(b) of FIG. 3 illustrates that two UVC LED elements are mounted on the handheld scanner main body 310. Referring to (b) of FIG. 3, similarly to (a) of FIG. 3, the handheld scanner main body 310 may include the coupling portion 311 onto which the tip is mounted. A UVC LED element may be mounted at the position 313 adjacent to the coupling portion 311. In an embodiment, a UVC LED element may be arranged at an angle and direction toward an optical module (not shown) of the handheld scanner main body 310. The UVC LED element may be arranged toward the optical module at the position 313 adjacent to the coupling portion 311 to irradiate UVC in a direction of the optical module. In addition, as shown in (b) of FIG. 3, a UVC LED element may be included in the position 315 near the fan of the handheld scanner main body 310. The UVC LED element may be arranged at the position 315 near the fan to irradiate UVC toward the inside of the handheld scanner main body 310. The UVC projected by the UVC LED element may sterilize air, the surfaces of the constituent elements inside the handheld scanner main body 310, and/or the frame 317 while moving into the handheld scanner main body 310 together with air introduced through the fan.

As such, according to an embodiment, at least one UVC LED element may be arranged in the handheld scanner main body 310 to effectively remove contaminants that are likely to be included in the surfaces of constituent elements included in the handheld scanner main body 310 or air introduced from the outside.

Figure 4:
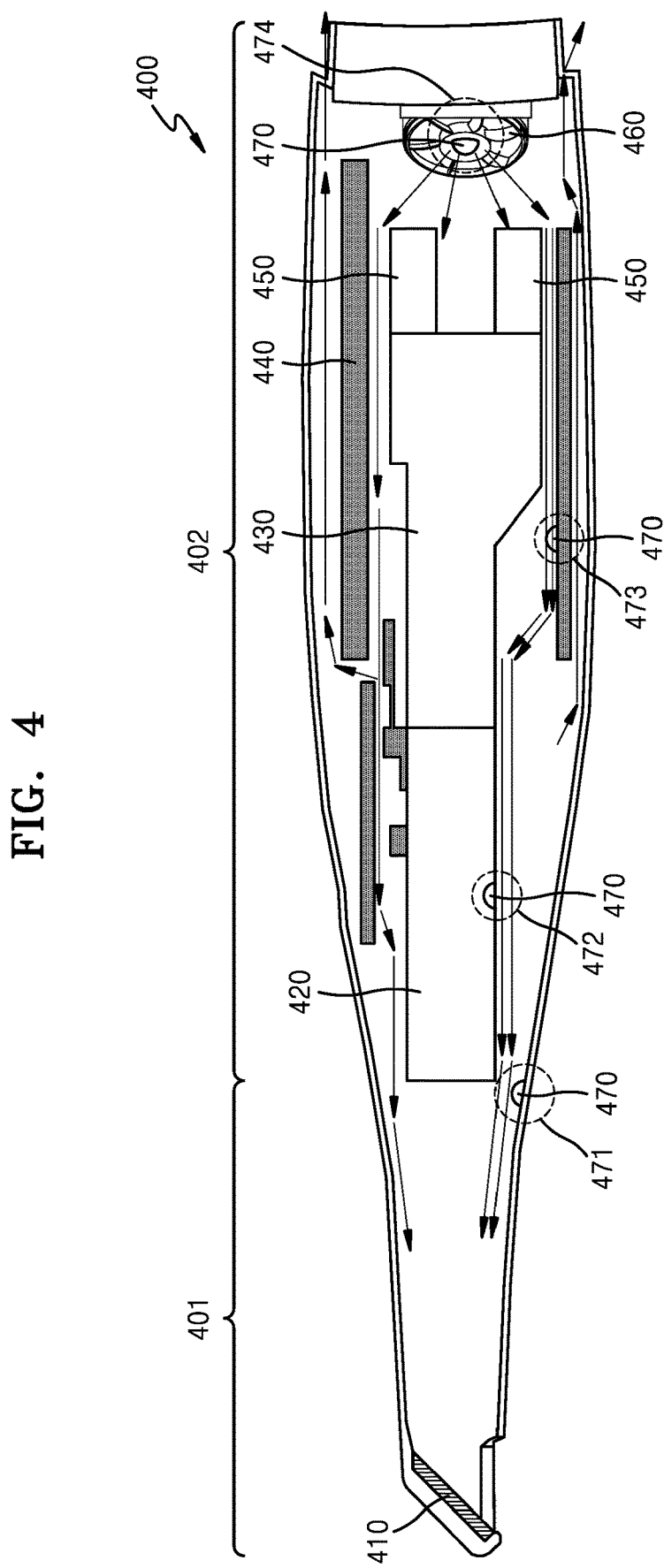
FIG. 4 is a cross-sectional view of the inside of a handheld scanner according to an embodiment.

FIG. 4 is a cross-sectional view of the inside of a handheld scanner according to an embodiment.

A handheld scanner 400 of FIG. 4 may be an example of the handheld scanner 100 of FIG. 1.

As described above, the handheld scanner 400 may include a main body 402 and a tip 401 provided to be detachable from the main body 402 and mounted on the main body 402.

Referring to FIG. 4, the main body 402 of the handheld scanner 400 may include an optical module 420, a projector 430, a printed circuit board (PCB) 440, a heat sink 450, a fan 460, and a UVC LED element 470.

One end of the tip 401 may include a coupling portion coupled to the main body 402, and the other end of the tip 401 may include an opening. The opening may be formed in one direction orthogonal to a length direction of the tip 401. Light projected by the projector 430 may leak through the opening, and light reflected from an object may flow into the optical module 420. A light path changing unit 410 may be arranged in the opening. The light path changing unit 410 may reflect light emitted from the projector 430 along a certain path such that the light is projected toward an object. In addition, the light path changing unit 410 may adjust a light path such that light reflected from an object and incident on the opening of the tip 401 is directed to a lens of a camera included in the optical module 420. The light path changing unit 410 may be a mirror or lens for performing the above-described role, but is not limited thereto, and may be any unit capable of changing a light path, for example, refracting or reflecting incident light.

The optical module 420 may include at least one camera that receives light reflected from an object. A camera may include at least one lens. For example, the lens included in the camera may be a pair of lenses respectively corresponding to a right field of view and a left field of view. The lenses may be arranged apart from each other to pass light incident through the opening through different paths. Light transmitted through the lens through a polarization filter may be received through an imaging sensor provided on an imaging board. The lenses may obtain an R image corresponding to the right field of view and an L image corresponding to the left field of view, respectively. The imaging sensor may be, for example, an element that converts light into digital data, such as a complementary metal oxide semiconductor (CMOS) image sensor. The imaging sensor may generate image information about an object, that is, image data. In other words, the imaging sensor may reconstruct the R image and the L image into three-dimensional image frames representing a surface of an object. A method of constructing a three-dimensional image frame is not limited thereto.

The projector 430 may project light onto an object. The projector 430 may project a specific type of light toward an object. In this state, a wavelength of the projected light may be, for example, a wavelength of a visible light region, but is not limited thereto.

The projector 430 may project patterned light onto an object and scan the object onto which the patterned light is projected, to obtain three-dimensional data representing the shape of the object. To this end, the projector 430 may allow light generated from a light source to be formed in the form of structured light having a specific pattern. The projector 430 may use a patterned mask or a digital micromirror device (DMD) to form a certain pattern.

The PCB 440 is a printed circuit board, and may mean a circuit board for connecting and fixing an electronic component terminal to the inside of the main body 402 of the handheld scanner 400. The PCB 440 may be a circuit board in which various electronic elements/components, such as integrated circuits (IC) and resistors, are assembled, arranged, and mounted on an insulating substrate of phenolic resin or epoxy resin, which is a plastic material, and a copper (Cu) processed conductor connection path (pattern) is formed.

The heat sink 450 may be attached to prevent an increase in temperature of the handheld scanner 400. The heat sink 450 may be formed to have a structure that absorbs heat generated from components or elements of the handheld scanner 400 and dissipates the heat to the outside.

The fan 460 is a kind of cooler, and may be a device that circulates air inside the main body 402 of the handheld scanner 400, reduces heat generated from components inside the main body 402 of the handheld scanner 400, and prevents dust from accumulating. The fan 460 has a structure in which small rotary blades rotate rapidly, and is installed at the end of the handheld scanner 400 to introduce outside air into the main body 402 of the handheld scanner 400 and allow the introduced air to move.

In FIG. 4, arrows indicate a moving direction of air. Outside air introduced by the fan 460 may move in directions of the arrows. The outside air may cool heat generated from components included in the handheld scanner 400 while moving along gaps created between components inside the handheld scanner 400. Most of the introduced outside air may be exhausted toward the sides of the fan 460, whereas some of the introduced outside air may be exhausted toward the sides of the tip 401.

In an embodiment, the handheld scanner 400 may include the UVC LED element 470. FIG. 4 illustrates, as an embodiment, that the handheld scanner 400 includes four UVC LED elements 470, but this is merely exemplary, and the handheld scanner 400 may include only one UVC LED element 470, two UVC LED elements 470, or three UVC LED elements 470. Alternatively, the handheld scanner 400 may include more than four UVC LED elements 470.

In an embodiment, a position at which a UVC LED element is arranged in the handheld scanner 400 may be determined by considering at least one of whether there is a space to mount the UVC LED element inside the handheld scanner 400, whether the position is where a sterilization effect is greater than or equal to a reference value when the UVC LED element is mounted, whether the position is in a path where an amount of air movement is greater than or equal to a reference value, and whether the position is where UVC projected from the UVC LED element is not likely to flow into a patient's oral cavity through the tip 401.

FIG. 4 illustrates, as an embodiment, that the UVC LED elements 470 are arranged at the front of the main body 402 of the handheld scanner 400, that is, a first position 471 adjacent to the coupling portion, a second position 472 adjacent to the optical module 420, a third position 473 adjacent to the projector 430, and a fourth position 474 adjacent to the fan 460, respectively.

In an embodiment, the UVC LED element 470 may be arranged at the first position 471 adjacent to the coupling portion of the handheld scanner 400. The tip 401 is introduced into a patient's oral cavity and thus is particularly sensitive to hygiene. Even in a case where an amount of air exhausted in a direction of the tip 401 is small and the tip 401 is sterilized, when air exhausted from the main body 402 to the tip 401 is contaminated, the possibility of introduction of contaminated air into an oral cavity may not be completely eliminated. Therefore, in an embodiment, the UVC LED element 470 may be arranged at the first position 471 adjacent to the coupling portion coupled to the tip 401 to sterilize air that may flow into the tip 401 from the main body 402 of the handheld scanner 400. The UVC LED element 470 may irradiate UVC onto air exhausted through the tip 401 to sterilize air that is likely to flow into an oral cavity through the tip 401, thereby effectively removing various harmful substances that may be included in the air, such as bacteria, viruses, and other microorganisms.

The UVC LED element 470 may be arranged at the first position 471 adjacent to the coupling portion on a lower side of the main body 402 of the handheld scanner 400 to irradiate UVC toward an upper side thereof. However, this is merely exemplary, the UVC LED element 470 may be arranged at a position adjacent to the coupling portion on the upper side or side surface of the main body 402 of the handheld scanner 400 to irradiate UVC toward the lower side or opposite side surface thereof.

In an embodiment, the UVC LED element 470 may be arranged at the second position 472 near the optical module 420. For example, the UVC LED element 470 may be disposed on the PCB 440 mounted near the optical module 420 or may be arranged in the optical module 420. The UVC LED element 470 may be arranged at the second position 472 near the optical module 420 to irradiate UVC toward the optical module 420 or toward the inside of the optical module 420, thereby sterilizing a surface of the optical module 420, the periphery of the optical module 420, and/or air inside the optical module 420. The UVC projected by the UVC LED element 470 may sterilize constituent elements included in the optical module 420, for example, surfaces of the camera, the lens included in the camera, the imaging board, and the imaging sensor, and air between these constituent elements. The UVC LED element 470 may be arranged at the second position 472 near the optical module 420 on the lower side of the main body 402 of the handheld scanner 400 to irradiate UVC toward the upper side thereof, but this is merely exemplary, and the UVC LED element 470 may be arranged at a position adjacent to the optical module 420 on the upper side or side surface of the main body 402 of the handheld scanner 400 to irradiate UVC toward the lower side or opposite side surface thereof.

In an embodiment, the UVC LED element 470 may be arranged at the third position 473 near the projector 430. The UVC LED element 470 may be arranged at the third position 473 near the projector 430 to irradiate UVC toward the projector 430. For example, the UVC LED element 470 may be disposed on the PCB 440 mounted near the projector 430 or may be arranged inside of the projector 430. The UVC LED element 470 may irradiate UVC toward a patterned mask or a DMD, included in the projector 430, to sterilize a surface of the projector 430 and/or air around the projector 430. The UVC LED element 470 may be arranged at the third position 473 near the projector 430 on the lower side of the main body 402 of the handheld scanner 400 to irradiate UVC toward the upper side thereof, or may be arranged at a position adjacent to the projector 430 on the upper side or side surface of the main body 402 of the handheld scanner 400 to irradiate UVC toward the lower side or opposite side surface thereof.

In an embodiment, the UVC LED element 470 may be arranged at a position where an amount of air, that is, a flow rate thereof, is greater than or equal to a reference value, to sterilize air. The position where the flow rate thereof is greater than or equal to the reference value may be, for example, near the fan 460. In an embodiment, the UVC LED element 470 may be arranged at the fourth position 474 adjacent to the fan 460. The UVC LED element 470 may be disposed on the PCB 440 mounted near the fan 460, etc., to irradiate UVC toward the outside air drawn in through the fan 460. The UVC LED element 470 may be arranged at a position adjacent to the fan 460 in a direction of the lower side, upper side, or side surface of the main body 402 of the handheld scanner 400. Alternatively, the UVC LED element 470 may be arranged to face a direction in which air is introduced by the fan 460 of the handheld scanner 400, to irradiate UVC toward the air introduced through the fan 460. The UVC LED element 470 may be arranged at the fourth position 474 adjacent to the fan 460 to sterilize outside air while the outside air is drawn into the handheld scanner 400 through the fan 460. Therefore, even when contaminated outside air is introduced, the handheld scanner 400 may remove contaminants rapidly. Therefore, only clean air from which various harmful substances are removed circulates inside the handheld scanner 400.

However, this is merely exemplary, and even when the UVC LED element 470 is not arranged near the fan 460, the UVC LED element 470 may be arranged at a position where a flow rate of air is greater than or equal to a reference value, to sterilize air.

In an embodiment, the constituent elements included in the handheld scanner 400 may be formed of components capable of reflecting UVC. For example, the constituent elements included in the handheld scanner 400, such as the optical module 420, the projector 430, the PCB 440, and the heat sink 450, a frame surrounding the main body 402 of the handheld scanner 400, and the like may be made of a material having a reflector effect. The material having the reflector effect may include metal. In an embodiment, the metal may be stainless steel. The stainless steel is a steel material including large amount of nickel and chromium, which may reflect UVC. Alternatively, in an embodiment, the metal may be polished aluminum. The polished aluminum may act as a reflector depending on a polishing method or the like.

Alternatively, in an embodiment, the constituent elements included in the handheld scanner 400 and the inside of the frame may be coated with white plaster or white water-based paint to reflect UVC.

UVC projected by the UVC LED element may be reflected by the constituent elements having reflection components inside the handheld scanner 400 or the inside of the frame. UVC may be projected onto the constituent elements included in the handheld scanner 400 and the frame to sterilize the constituent elements and a surface of the frame, and may be reflected from the surface into the air to sterilize the surrounding air. UVC projected by the UVC LED element may be reflected from a surface of a constituent element and projected onto a surface of another component to sterilize the surface of the other component.

Figure 5:
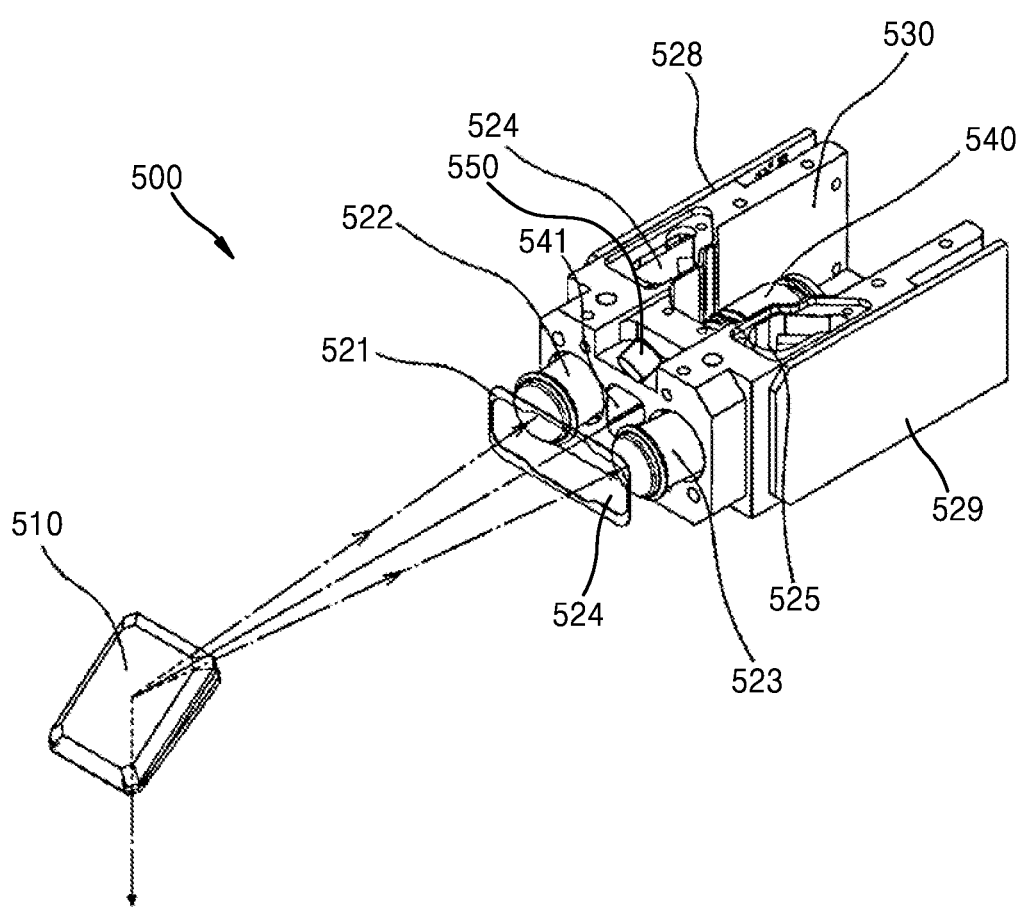
FIG. 5 is an exploded perspective view of an optical module and a projector, included in a handheld scanner according to an embodiment.

FIG. 5 is an exploded perspective view of an optical module and a projector, included in a handheld scanner according to an embodiment.

Referring to FIG. 5, light incident through an opening included in a tip of a handheld scanner 500 may be reflected by a light path changing unit 510 and transmitted to at least one of lenses 522 and 523 through a polarization filter 521. At least one of the lenses 522 and 523 may be connected to a stationary camera mounting portion 530. The camera mounting portion 530 may form a light waveguide. The light waveguide may be provided such that incoming light incident from the opening and emitted light projected from a projector 540 are separated from each other and do not affect each other. The light waveguide may include an emitted light path portion 541 providing a light path for the emitted light projected from the projector 540, and incoming light path portions 524 and 525 providing a light path for the incoming light incident through at least one of the lenses 522 and 523. Imaging boards 528 and 529 may be integrated with an imaging sensor to generate image data about an object.

In an embodiment, an UVC LED element 550 may be arranged in a space around the emitted light path portion 541. The UVC LED element 550 may irradiate UVC in a direction of the polarization filter 521 such that the irradiated UVC may pass through the polarization filter 521 and move in a direction of the light path changing unit 510. The UVC projected by the UVC LED element 550 may sterilize air in a space between the polarization filter 521 and the light path changing unit 510. In this case, as the sterilized air moves to the periphery of the light path changing unit 510, air that may be introduced from a main body of the handheld scanner 500 to the tip may also be sterilized.

In an embodiment, the UVC LED element 550 may be included in the projector 540. In this case, the projector 540 may further include the UVC LED element 550, in addition to an LED used as a light source.

In an embodiment, when the handheld scanner 500 operates in a scan mode, a light source (for example, an RGB light source) included in the projector 540 may project light, and a camera may obtain an image of an object through at least one lens. When the UVC LED element operates while the handheld scanner 500 scans an object, there is a possibility that precise three-dimensional scan data may not be obtained due to UVC.

In an embodiment, while the handheld scanner 500 scans an object, the UVC LED element 550 may be controlled not to operate. In other words, while an RGB light source included in the projector 540 of the handheld scanner 500 is turned on and projects light, the UVC LED element 550 may be controlled to be turned off.

While the UVC LED element 550 is turned on, the handheld scanner 500 may be controlled not to obtain a two-dimensional image of an object. In other words, a two-dimensional image of an object may not be generated from incoming light incident through the at least one lens of the lenses 522 and 523 while the UVC LED element 550 included in the handheld scanner 500 is turned on. Alternatively, while the UVC LED element 550 is turned on, the handheld scanner 600 may be controlled such that a two-dimensional image generated from incoming light incident through the at least one of the lenses 522 and 523 is not used when a three-dimensional oral cavity model is generated.

In an embodiment, the polarization filter 521 may be made of a material capable of transmitting ultraviolet light. For example, the polarization filter 521 may be formed of quartz glass including a large amount of silicon dioxide, but is not limited thereto, and the polarization filter 521 may be formed of various materials capable of transmitting UVC.

Figure 6:
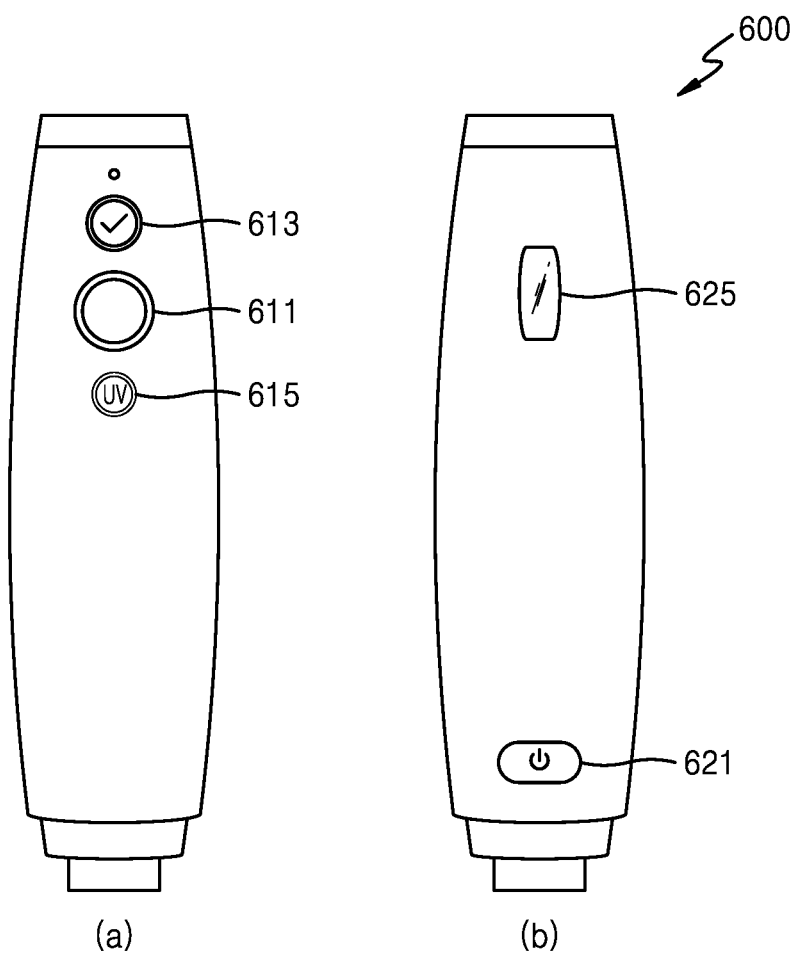
FIG. 6 is a view of the appearance of a handheld scanner according to an embodiment.

FIG. 6 is a view of the appearance of a handheld scanner according to an embodiment.

In an embodiment, each of (a) of FIG. 6 and (b) of FIG. 6 illustrates a handheld scanner 600 having a different appearance.

Referring to FIG. 6, a frame or case surrounding the handheld scanner 600 may include a user input unit for controlling the handheld scanner 600. A user may control the operation of the handheld scanner 600 by using the user input unit.

The user input unit may include a control button for controlling the handheld scanner 600. The control button may include a power button for controlling power of the handheld scanner 600. The power button may receive a user input for turning on/off power of the handheld scanner 600. The handheld scanner 600 may be turned on or turned off according to a user input through the power button. In addition, the user input unit may include a mode button for controlling an operation mode of the handheld scanner 600.

Referring to (a) of FIG. 6, the user input unit included in the handheld scanner 600 may include a control button 611 and a mode button 613. The control button 611 may include a physical button for receiving a push manipulation by a user or a touch button displayed on a touchpad for sensing a touch. In an embodiment, the control button 611 may be used as a power button for controlling power of the handheld scanner 600.

Alternatively, the control button 611 may be a communication module that receives a control signal from a remote controller (not shown). The control button 611 may receive a control signal from the remote controller by using infrared or Bluetooth low energy (BLE) communication. A user may remotely control functions of the handheld scanner 600 by transmitting a control signal to the control button 611 by using at least one of a key or button provided in the remote controller, a touchpad, a microphone (not shown) capable of receiving the user's voice, and a sensor (not shown) capable of recognizing the motion of the controller.

In an embodiment, the handheld scanner 600 of (a) of FIG. 6 may further include the mode button 613 that receives a user input for controlling an operation mode of the handheld scanner 600. The handheld scanner 600 may operate in a scan mode or a UVC LED element operation mode according to a user input through the mode button 613. The UVC LED element operation mode may refer to a mode in which power of a UVC LED element is turned on and irradiates UVC in a standby mode state.

Similarly to the control button 611, the mode button 613 may include a touch button or physical button that receives a touch or physical input from a user.

In another embodiment, as shown in (b) of FIG. 6, the handheld scanner 600 may include only one power button 621. The handheld scanner 600 may perform all of power on/off and mode change functions through the power button 621. In order to receive a user input for power on/off and a user input for a mode change of the handheld scanner 600 by using one button, the handheld scanner 600 may identify whether a user input is for power on/off or a mode change.

For example, the handheld scanner 600 may identify the duration of a touch or physical push on a button, and thus, when a button input is a long-pressed input, identifies the input as a user input for power on/off, and when a button input is a short-pressed input, identifies the input as a user input for a mode change.

Alternatively, the handheld scanner 600 may recognize user inputs through the power button 621 as different control signals according to current operating conditions, and accordingly the operation of the handheld scanner 600 may be controlled. For example, when receiving a user input through the power button 621 in a state where the handheld scanner 600 is powered off, the handheld scanner 600 may be powered on. Afterwards, when receiving the user input through the power button 621 again, the handheld scanner 600 may operate in a scan mode. When receiving the user input through the power button 621 again while the handheld scanner 600 operates in the scan mode, the handheld scanner 600 may change the current mode to a UVC LED element operation mode of a standby mode. When the handheld scanner 600 receives the user input through the power button 621 while a UVC LED element operates, both the UVC LED element and the handheld scanner 600 may be powered off.

In an embodiment, in a power-on state, the handheld scanner 600 may operate in a scan mode or a standby mode depending on whether a constituent element included in the handheld scanner 600 operates.

In an embodiment, the handheld scanner 600 may operate in a scan mode. The scan mode may mean a mode in which all constituent elements of the handheld scanner 600 are activated and normally operate. A user, such as a dentist, may obtain raw data or a three-dimensional intraoral image by scanning a patient's oral cavity while the handheld scanner 600 operates in the scan mode.

In an embodiment, the handheld scanner 600 may operate in a standby mode. The standby mode may mean a state in which the handheld scanner 600 itself is powered on, but an optical portion included in the handheld scanner 600, that is, an optical module and a projector, is deactivated. In the standby mode, the optical portion may be in a standby state. In the standby mode, constituent elements other than the optical portion may be in an active state. For example, in the standby mode, a communication module (not shown) may perform a network function, and may receive a control signal from an external device, for example, a data processing device or a remote controller, or may transmit/receive information about operating conditions of the handheld scanner 600 to/from the data processing device. The standby mode may also be referred to as an idle mode.

In an embodiment, the handheld scanner 600 may automatically enter a standby mode when not receiving a control signal from a user for a certain period of time. Alternatively, in an embodiment, the handheld scanner 600 may enter a standby mode when a preset scan time elapses while the handheld scanner 600 operates in a scan mode, or even when a scan mode off command is received from a user.

In an embodiment, the handheld scanner 600 may include one or more UVC LED elements (not shown). A UVC LED element is an LED light source that irradiates UVC, and may have a small size so as to be efficiently mounted in a small device, such as a handheld scanner. For example, the UVC LED element may be of a small point light source type.

In an embodiment, while the handheld scanner 600 operates in a standby mode, one or more UVC LED elements may be turned on to irradiate UVC. In an embodiment, while operating in a scan mode, the handheld scanner 600 may control a UVC LED element not to operate. UVC has sterilizing power which is strong enough to destroy the molecular structure of DNA or RNA of organism cells. Thus, when the body is exposed to UVC, UVC may adversely affect the body. For example, when UVC is in direct contact with the skin, the skin may get burnt, and when the eye is exposed to UVC, the retina may be damaged. In addition, UVC may interfere with obtaining of precise scan data about an object. Therefore, in order to prevent UVC from being projected while a patient's oral cavity is scanned using the handheld scanner 600, in an embodiment, one or more UVC LED elements may be turned on only while the handheld scanner 600 operates in a standby mode, and all of UVC LED elements may be turned off while the handheld scanner 600 operates in a scan mode.

In an embodiment, the handheld scanner 600 may allow a UVC LED element to be turned on whenever the handheld scanner 600 enters a standby mode. For example, when the handheld scanner 600 receives a user input through the control button 611 or the power button 621 in a power-off state, the handheld scanner 600 is powered on and simultaneously enters a standby mode, and one or more UVC LED elements may be automatically turned on.

In an embodiment, when a mode of the handheld scanner 600 is changed from a scan mode to a standby mode, the handheld scanner 600 may simultaneously or sequentially allow one or more UVC LED elements to be powered on. For example, the handheld scanner 600 may enter a standby mode when not receiving a control signal from a user for a certain period of time. The handheld scanner 600 enters the standby mode and simultaneously enters a UVC LED element operation mode, such that a UVC LED element may be powered on.

Alternatively, in another embodiment, when a preset time elapses after the handheld scanner 600 enters a standby mode, the handheld scanner 600 may allow a UVC LED element to be automatically turned on. For example, in a case where the handheld scanner 600 automatically enters a standby mode because a user does not operate the handheld scanner 600 for a certain period of time, when a preset time elapses after the handheld scanner 600 enters the standby mode, one or more UVC LED elements may be automatically powered on.

In an embodiment, as shown in FIG. 6, the frame or case surrounding the handheld scanner 600 may further include an indicator 615 or 625 for indicating whether a UVC LED element is in operation. The indicator 615 or 625 may indicate whether a UVC LED element is in operation, by using various methods, such as light color, light flickering, text color, for example, a change in color of text "UV", vibration, or sound. Alternatively, the indicator 615 or 625 may be implemented as a transparent window through which the inside of the handheld scanner 600 may be seen. Since UVC has an invisible wavelength of ultraviolet light, the handheld scanner 600 may further include an LED that projects light of a specific color, for example, blue light or red light, aside from the UVC LED element. The handheld scanner 600 may allow the LED of the specific color to be turned on while the UVC LED element is turned on, and may allow the LED of the specific color to be turned off while the UVC LED element is turned off. A user may identify whether the UVC LED element is in operation, by recognizing light of a specific color projected from the inside of the handheld scanner 600 through the transparent window.

In an embodiment, when the handheld scanner 600 receives a user input to power off the handheld scanner 600 through the control button 611 or the power button 621 while one or more UVC LED elements operate, the UVC LED elements may be turned off. In addition, in an embodiment, when the handheld scanner 600 receives a user input to operate in a scan mode through the mode button 613 or the power button 621 while one or more UVC LED elements operate, the UVC LED elements may be turned off, and the handheld scanner 600 may operate in the scan mode. In this case, a user may identify that the UVC LED elements are turned off by using the indicator 615 or 625 included in the handheld scanner 600.

Alternatively, in another embodiment, (a) of FIG. 6 and (b) of FIG. 6 may illustrate the front and back of one handheld scanner, rather than different handheld scanners. In other words, the handheld scanner 600 may have a shape shown in (a) of FIG. 6 as a front portion of the handheld scanner 600, and may have a shape shown in (b) of FIG. 6 as a rear portion of the handheld scanner 600. In this case, the handheld scanner 600 may include the control button 611 and the mode button 613 on the front portion, and may include the power button 621 on the rear portion.

The handheld scanner 600 may receive a power on/off command from a user through the power button 621 provided on the rear portion. The handheld scanner 600 may receive a control signal through the control button 611 provided on the front portion. In this case, the control button 611 may not operate as a power button, but may be used to receive only a control signal from the remote controller. The handheld scanner 600 may change a mode of the handheld scanner 600 according to a user input through the mode button 613.

Figure 7:
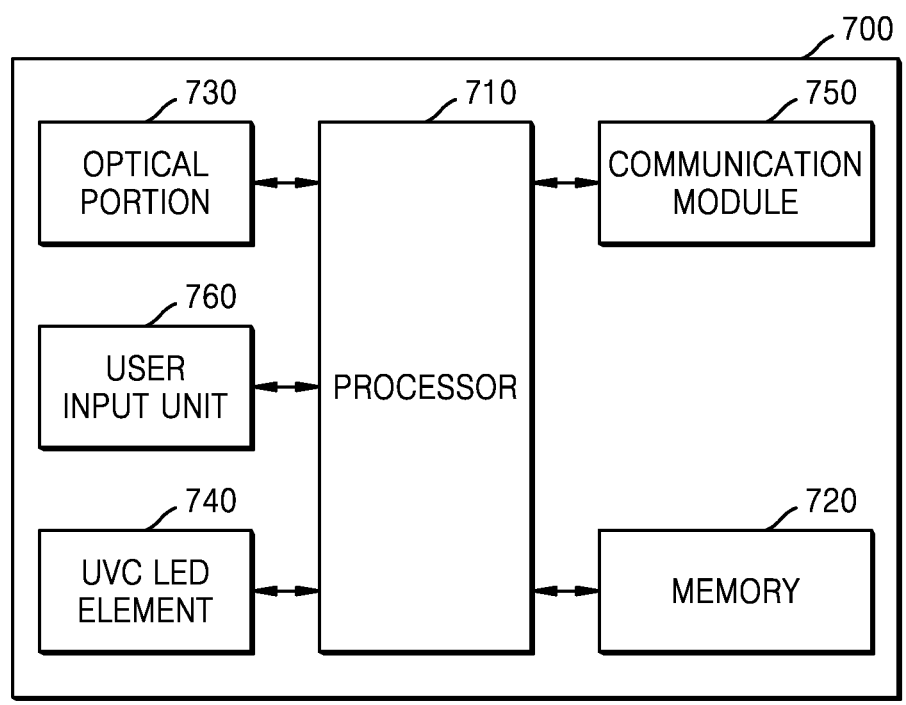
FIG. 7 is an internal block diagram of a handheld scanner according to an embodiment.

FIG. 7 is an internal block diagram of a handheld scanner according to an embodiment.

Referring to FIG. 7, a handheld scanner 700 may include a processor 710, a memory 720, an optical portion 730, a UVC LED element 740, a communication module 750, and a user input unit 760.

The memory 720 may store at least one instruction. In addition, the memory 720 may store at least one instruction to be executed by the processor 710. In addition, the memory 720 may store at least one program to be executed by the processor 710.

The optical portion 730 may include an optical module and a projector. The optical portion 730 may include a light source, a projector that projects light from the light source, and at least one camera that receives light reflected from an object. The optical portion 730 may project patterned light or structured light. The optical portion 730 may project light using the light source and form a pattern by controlling each of fine mirrors included in a DMD. The optical portion 730 may project light by controlling the mirrors included in the DMD to be turned on or off. The optical portion 730 may project light to an object and scan the object onto which the light is projected, to obtain three-dimensional data representing the shape of the object.

In an embodiment, the handheld scanner 700 may include one or more UVC LED elements 740. The UVC LED element 740 may be an LED that irradiates UVC.

The communication module 750 may communicate with a data processing device through a wired or wireless communication network.

In an embodiment, the communication module 750 may receive a control signal from the data processing device. In addition, the communication module 750 may transmit information about an operational state of the handheld scanner 700 to the data processing device. In addition, the communication module 750 may communicate with the data processing device under the control by the processor 710 and transmit raw data obtained by the optical portion 730 to the data processing device.

The communication module 750 may include at least one short-range communication module that performs communication according to communication standards, such as Bluetooth, Wi-Fi, BLE, NFC/RFID, Wi-Fi Direct, UWB, or ZigBee, a long-range communication module that communicates with a server for supporting long-range communication according to long-range communication standards, and at least one port to be connected to an external electronic device by a wired cable, to communicate with the external electronic device by wire.

The user input unit 760 may receive a user input for controlling the handheld scanner 700. The user input unit 760 may include a touch panel for sensing a touch by a user, a button for receiving a push manipulation by a user, a voice recognition device including a microphone, and the like. Alternatively, the user input unit 760 may further include at least one of a wheel for receiving a rotation manipulation by a user or a dome switch, and a sensor (not shown) capable of motion recognition. The user input unit 760 may receive one or more of a power on/off command for the handheld scanner 700, and a command to change a mode of the handheld scanner 700 to a scan mode or a UVC LED element operation mode.

The processor 710 may generally control the handheld scanner 700. The processor 710 may control at least one of constituent elements included in the handheld scanner 700 to perform a desired operation. Therefore, when the processor 710 performs certain operations, the processor 710 controls at least one of components included in the handheld scanner 700 to perform certain operations. The processor 710 may control the optical portion 730 to obtain three-dimensional data about an object.

In an embodiment, the processor 710 may control the UVC LED element 740 to turn the UVC LED element 740 on or off.

In an embodiment, the processor 710 may control the UVC LED element to be turned on in response to detecting a first event. The first event may include one or more of receiving a first control signal through the user input unit 760 and receiving a first control signal from the data processing device through the communication module 750. The first control signal may include at least one of a scan mode off command, a power on command for the handheld scanner 700, and a power on command for the UVC LED element 740.

The handheld scanner 700 may perform an error correction operation, that is, calibration, frequently or at regular intervals to obtain accurate three-dimensional model data. In an embodiment, when the calibration of the handheld scanner 700 ends, the processor 710 may recognize that the first event has occurred, and the UVC LED element 740 may be turned on.

In an embodiment, the processor 710 may detect, as the first event, entering the handheld scanner 700 into a standby mode. When the handheld scanner 700 enters the standby mode, the processor 710 may allow the UVC LED element 740 to be turned on.

In an embodiment, the processor 710 may detect, as the first event, elapsing of a preset time after the handheld scanner 700 enters a standby mode. When the handheld scanner 700 enters the standby mode and the preset time elapses, the processor 710 may allow the UVC LED element 740 to be turned on.

In an embodiment, the processor 710 may control the UVC LED element 740 to be turned off in response to detecting a second event while the UVC LED element 740 is turned on. The detection of the second event may include one or more of receiving a second control signal through the user input unit 760 and receiving a second control signal from the data processing device through the communication module 750. The second control signal may include at least one of a scan mode entry command, a power off command for the handheld scanner 700, and a power off command for the UVC LED element 740.

In an embodiment, the processor 710 may prevent the UVC LED element 740 from operating while the handheld scanner 700 operates in a scan mode.

In an embodiment, the processor 710 may prevent the light source included in the projector inside the handheld scanner 700 and the UVC LED element 740 from operating at the same time.

In an embodiment, the processor 710 may prevent a camera inside the handheld scanner 700 from obtaining a two-dimensional image of an object while the UVC LED element 740 operates.

Alternatively, in an embodiment, the processor 710 may prevent a two-dimensional image of an object, which is obtained by a camera inside the handheld scanner 700 while the UVC LED element 740 operates, from being used when a three-dimensional oral cavity model is generated. In an embodiment, the processor 710 detect, as a second event, a case where the UVC LED element 740 is turned on to irradiate UVC and a preset time elapses. The processor 710 may allow the UVC LED element 740 to be automatically turned off after the UVC LED element 740 irradiates UVC for the preset time.

The handheld scanner 700 is an electronic device in which various electronic components are embedded, and an operating temperature suitable for scanning is set. When scanning is performed out of the operating temperature, the efficiency of scanning is reduced. Therefore, the handheld scanner 700 is preheated before scanning, such that the inner temperature becomes the appropriate operating temperature.

The temperature of the UVC LED element 740 may increase when the UVC LED element 740 is turned on due to characteristics of UVC LED chips. Therefore, when the UVC LED element 740 is turned on, the temperature inside the handheld scanner 700 may also increase. In an embodiment, the processor 710 may allow a preheating operation performed before scanning to be omitted when the UVC LED element 740 operates for a certain period of time. Alternatively, the processor 710 may allow preheating to be performed only for a time shorter than a preset preheating time.

Figure 8:
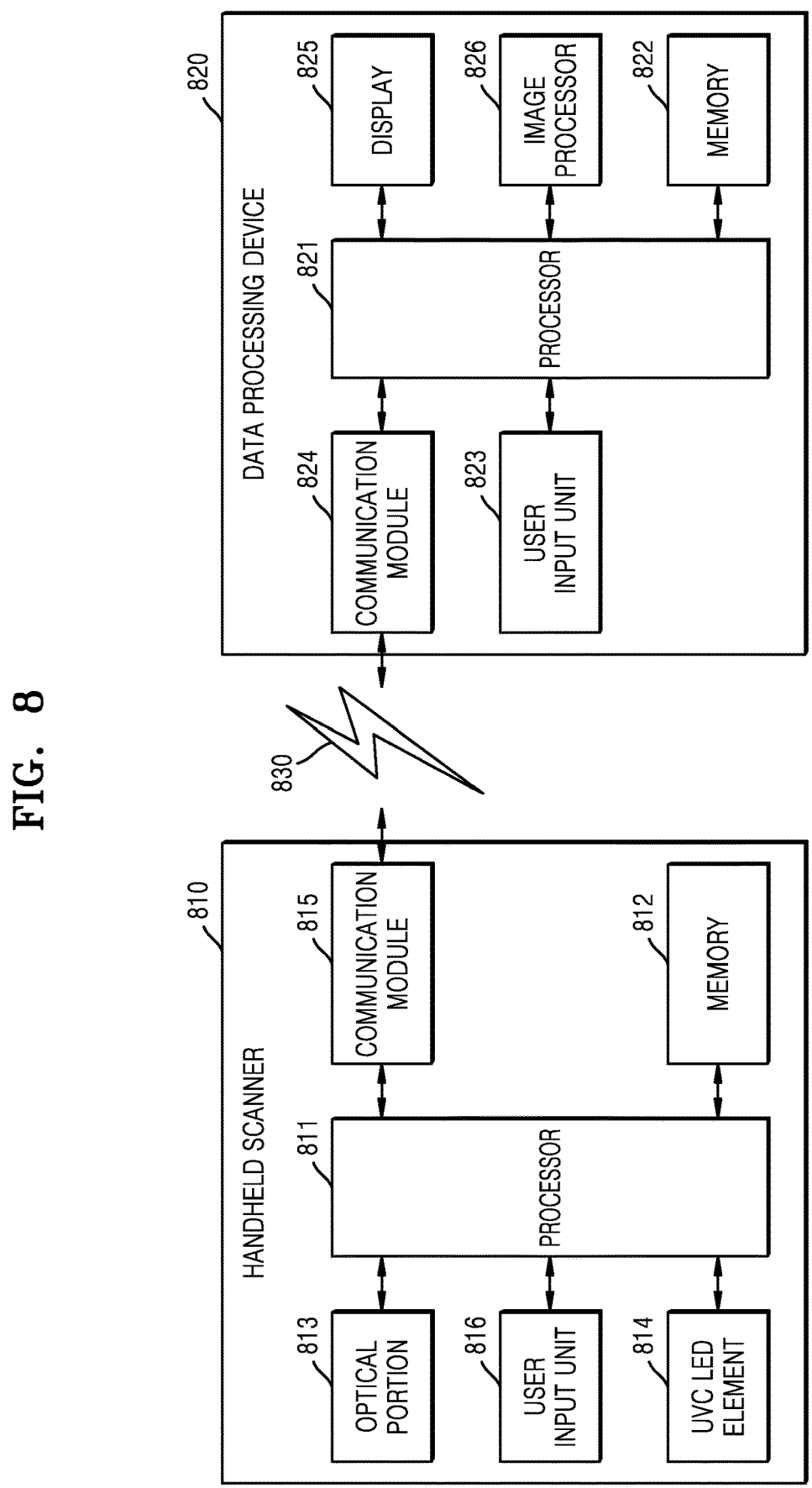
FIG. 8 is an example of a detailed block diagram of an image processing system including a handheld scanner and a data processing device.

FIG. 8 is an example of a detailed block diagram of an intraoral image processing system including a handheld scanner and a data processing device.

In an embodiment, an intraoral image processing system may include a handheld scanner 810, a data processing device 820, and a communication network 830.

The handheld scanner 810 may transmit raw data, which is obtained by scanning a patient's oral cavity or a tooth cast model, to the data processing device 820 through the communication network 830, or may process raw data to generate a three-dimensional virtual model and transmit the three-dimensional virtual model to the data processing device 820.

The handheld scanner 810 may include a processor 811, a memory 812, an optical portion 813, a UVC LED element 814, a communication module 815, and a user input unit 816. The handheld scanner 810 of FIG. 8 is an example of the handheld scanner 700 of FIG. 7, and the processor 811, the memory 812, the optical portion 813, the UVC LED element 814, the communication module 815, and the user input unit 816 may correspond to the processor 710, the memory 720, the optical portion 730, the UVC LED element 740, the communication module 750, and the user input unit 760, included in the handheld scanner 700 of FIG. 7, respectively. Hereinafter, redundant descriptions are omitted.

The processor 811 may generally control the handheld scanner 810.

In an embodiment, the processor 811 may receive a control signal from the user input unit 816, receive a control signal from the data processing device 820, and control the handheld scanner 810 according to a control signal.

In an embodiment, the processor 811 may transmit information about an operational state of the handheld scanner 810 or the like to the data processing device 820 through the communication network 830 in real time.

Hereinafter, the data processing device 820 is described. The data processing device 820 may be referred to as an intraoral image processing device.

The data processing device 820 may include a processor 821, a memory 822, a user input unit 823, a communication module 824, a display 825, and an image processor 826.

The user input unit 823 may receive a user input for controlling the data processing device 820. The user input unit 823 may include a user input device including a touch panel for sensing a touch by a user, a button for receiving a push manipulation by a user, a mouse or keyboard for assigning or selecting a point on a user input unit screen, and the like, and may include a voice recognition device for voice recognition.

In an embodiment, the user input unit 823 may receive an input of at least one of a power on command for the handheld scanner 810 and a power on command for the UVC LED element 814 included in the handheld scanner 810 from a user for controlling the data processing device 820.

The communication module 824 may communicate with at least one external electronic device through a wired or wireless communication network. The communication module 824 may communicate with the handheld scanner 810 under the control by the processor 821.

In detail, the communication module 824 may include at least one short-range communication module that performs communication according to communication standards, such as Bluetooth, Wi-Fi, BLE, NFC/RFID, Wi-Fi Direct, UWB, or ZigBee. In addition, the communication module 824 may further include a long-range communication module that communicates with a server for supporting long-range communication according to long-range communication standards.

In addition, the communication module 824 may include at least one port to be connected to an external electronic device, for example, the handheld scanner 810, by a wired cable.

In an embodiment, the communication module 824 may receive information about a current state of the handheld scanner 810 from the handheld scanner 810. In an embodiment, the communication module 824 may transmit a control signal to the handheld scanner 810. The control signal may include a first control signal including at least one of a power on command for the handheld scanner 810 and a power on command for the UVC LED element 814 included in the handheld scanner 810. In addition, the control signal may include a second control signal including a scan mode entry command for the handheld scanner 810, a power off command for the handheld scanner 810, and a power off command for the UVC LED element 814.

The display 825 may display a certain screen under the control by the processor 821. The display 825 may output a user interface screen for receiving a user input.

In an embodiment, a user may identify a current operational state of the handheld scanner 810 and select at least one of a power on command for the handheld scanner 810 and a power on command for the UVC LED element 814 included in the handheld scanner 810, by using a user interface screen output through the display 825. In addition, in an embodiment, the display 825 may output a user interface screen for receiving a selection of whether to perform UVC LED element auto-on.

the display 825 may display a screen including an intraoral image generated based on data obtained by scanning a patient's oral cavity or a plaster model of an oral cavity by using the handheld scanner 810. In addition, the display 825 may output a three-dimensional oral cavity model generated from two-dimensional image data received from the handheld scanner 810.

The image processor 826 may perform operations for generating and/or processing an image. In detail, the image processor 826 may receive raw data obtained from the handheld scanner 810 and generate a three-dimensional virtual model based on the received data.

The memory 822 may store at least one instruction. In addition, the memory 822 may store at least one instruction to be executed by the processor 821. In addition, the memory 822 may store at least one program to be executed by the processor 821. In addition, the memory 822 may store data (for example, raw data obtained through oral cavity scanning) received from the handheld scanner 810. Alternatively, the memory 822 may store an intraoral image three-dimensionally representing an oral cavity. According to an embodiment, the memory 822 may include one or more instructions for obtaining a three-dimensional oral cavity model from two-dimensional image data.

The processor 821 may control performing of a desired operation by executing at least one instruction stored in the memory 822. The at least one instruction may be stored in an internal memory included in the processor 821 or the memory 822 included in a data processing device, aside from the processor 821.

In an embodiment, the processor 821 may transmit a control signal to the handheld scanner 810 by executing one or more instructions stored in the memory 822, such that the handheld scanner 810 is controlled according to the control signal. The processor 821 may transmit a control signal selected by a user through the user input unit 823 to the handheld scanner 810 through the communication network 830, in response to a user interface screen output through the display 825. The processor 821 may control the UVC LED element 814 included in the handheld scanner 810 to be turned on or control the UVC LED element 814 to be turned off, by transmitting the control signal to the handheld scanner 810.

According to an embodiment, the performing of operations such as "extraction," "obtaining," "generating," and the like, by the processor 821, may include not only directly performing the above-described operations by executing at least one instruction in the processor 821, but also controlling other constituent elements to perform the above-described operations.

In order to implement the embodiments disclosed herein, the handheld scanner 810 and the data processing device 820 may include only some of the constituent elements illustrated in FIG. 8 or may include more constituent elements than the constituent elements illustrated in FIG. 8.

In addition, the data processing device 820 may store and execute dedicated software linked to the handheld scanner 810. The dedicated software may also be referred to as a dedicated program, a dedicated tool, or a dedicated application. When the data processing device 820 operates in conjunction with the handheld scanner 810, the dedicated software stored in the data processing device 820 may be connected to the handheld scanner 810 to receive, in real time, data obtained through oral cavity scanning.

In addition, the dedicated software may perform at least one of operations to transmit a control signal to the handheld scanner 810, and obtain, process, store, and/or transmit an intraoral image. The dedicated software may be stored in the processor 821. In addition, the dedicated software may provide a user interface screen for use of data obtained from a three-dimensional scanner. The user interface screen provided by the dedicated software may include a screen for selecting a control signal according to the disclosed embodiment, or a screen for receiving a selection of whether to perform UVC LED element auto-on.

Figure 9:
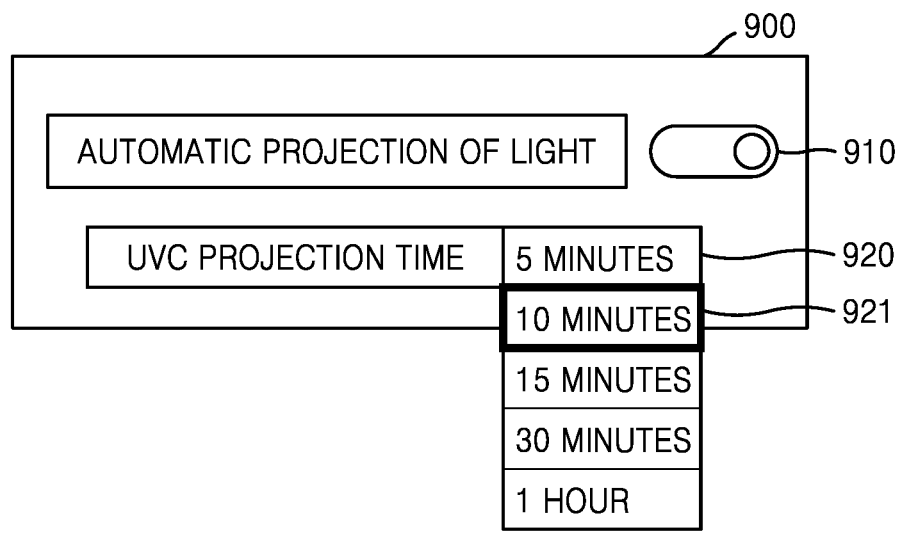
FIG. 9 illustrates that a data processing device outputs a user interface screen for receiving a selection of whether to perform automatic projection of UVC, according to an embodiment.

FIG. 9 illustrates that a data processing device outputs a user interface screen for receiving a selection of whether to perform automatic projection of UVC, according to an embodiment.

In an embodiment, a data processing device may receive, from a user, a selection of various setting information in relation to the operation of a UVC LED element.

In an embodiment, a data processing device may display a user interface screen 900 for receiving a selection of whether to perform automatic projection of UVC in relation to the operation of a UVC LED element, in the form of a text window on a partial area of a display. The size, output position, transparency, and/or shape of the user interface screen 900 for receiving a selection of whether to perform automatic projection of UVC may vary.

A user may select whether to perform automatic projection of UVC by seeing the user interface screen 900 and using a select button 910, to, when a first event occurs, allow a UVC LED element to be automatically turned on to irradiate UVC or prevent this function from being performed.

A data processing device may transmit a control signal to a handheld scanner when a user input to select automatic projection of UVC is received through the user interface screen 900, to allow UVC to be automatically projected whenever a first event is detected, and to stop UVC projection whenever a second event is detected during UVC projection.

The user interface screen 900 may further include a button 920 for receiving a selection of a UVC projection time. A user may see the user interface screen 900 and select 921 a time during which UVC is automatically projected, such that a UVC LED element may irradiate UVC for the selected time.

Figure 10:
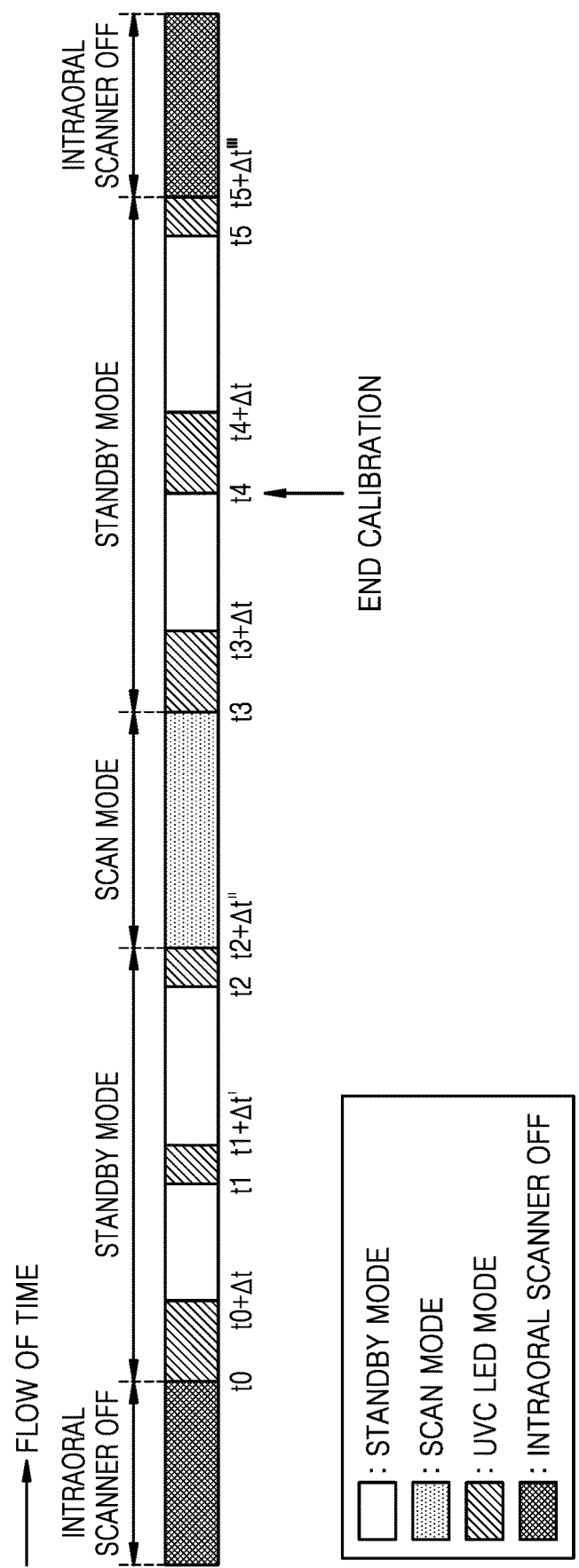
FIG. 10 is a view for explaining a timing of operation of a UVC LED element included in a handheld scanner, according to an embodiment.

FIG. 10 is a view for explaining a timing of operation of a UVC LED element included in a handheld scanner, according to an embodiment.

In an embodiment, the handheld scanner may control the UVC LED element to be turned on in response to detecting a first event.

In an embodiment, the first event may include at least one of receiving a first control signal through a user input unit and receiving a first control signal from a data processing device through a communication module. The first control signal may include at least one of a scan mode off command, a power on command for the handheld scanner, and a power on command for the UVC LED element.

In addition, in an embodiment, the first event may include at least one of a case where calibration of the handheld scanner ends, a case where the handheld scanner enters a standby mode, and a case where a preset time elapses after the handheld scanner enters the standby mode.

In an embodiment, the handheld scanner may control the UVC LED element to be turned off in response to detecting a second event while the UVC LED element is turned on.

In an embodiment, the second event may include at least one of receiving a second control signal through a user input unit and receiving a second control signal from a data processing device through a communication module. The second control signal may include at least one of a scan mode entry command, a power off command for the handheld scanner, and a power off command for the UVC LED element. In addition, in an embodiment, the second event may include the UVC LED element being turned on to irradiate UVC and elapsing of a preset time.

Hereinafter, referring to FIG. 10, it is described that the handheld scanner turns the UVC LED element on/off according to the occurrence of the first event or the second event.

Referring to FIG. 10, the handheld scanner is powered off before a time point of t0. When the handheld scanner is powered off, the UVC LED element included in the handheld scanner also does not operate.

The handheld scanner may receive a control signal for a power on command for the handheld scanner at the time point of t0. When the handheld scanner receives the control signal for the power on command for the handheld scanner from the user input unit or the data processing device included in the handheld scanner, the handheld scanner may be powered on and enters a standby mode.

In an embodiment, the handheld scanner may detect, as the first event, the receiving of the control signal for the power on command, and may allow the UVC LED element to be turned on at the time point of t0.

In an embodiment, when Δt elapses after the UVC LED element is turned on and the UVC LED element irradiates UVC for Δt, which is a certain amount of preset time, the handheld scanner may allow the UVC LED element to be automatically turned off at a time point of t+Δt. The handheld scanner may identify, as the occurrence of the second event, a case where the preset time elapses after the UVC LED element is turned on and then the UVC LED element irradiates UVC, and may allow the UVC LED element to be automatically turned off when the certain amount of preset time elapses.

In an embodiment, when a preset time, for example, a time of t1, elapses after the handheld scanner enters the standby mode, the handheld scanner may identify that the preset time has elapsed after entering the standby mode as the occurrence of the first event. The handheld scanner may allow the UVC LED element to be automatically turned on at a time point at which the preset time elapses after entering the standby mode.

In an embodiment, after the UVC LED element is turned on at a time point of t1, the handheld scanner may receive a control signal to turn off the UVC LED element from the user input unit or data processing device included in the handheld scanner at a time point of t1+Δt'. In an embodiment, when receiving the control signal to turn off the UVC LED element, the handheld scanner may identify the reception of the control signal to turn off the UVC LED element as the occurrence of the second event and allow the UVC LED element to be turned off at the time point of t1+Δt'.

In an embodiment, when receiving a control signal to turn on the UVC LED element from the user input unit or data processing device included in the handheld scanner at a time point of t2, the handheld scanner may identify the reception of the control signal to turn on the UVC LED element as the occurrence of the first event, and may allow the UVC LED element to be turned on at a time point at which the first event has occurred, that is, at the time point of t2.

In an embodiment, the handheld scanner may receive a control signal to enter a scan mode from the user input unit or data processing device included in the handheld scanner at a time point of t2+Δt". When receiving the control signal to enter the scan mode, the handheld scanner may identify the reception of the control signal to enter the scan mode as the occurrence of the second event. The handheld scanner may allow the UVC LED element to be turned off at the time point of t2+Δt" in response to the occurrence of the second event. In other words, in an embodiment, the handheld scanner may control the UVC LED element not to operate while operating in the scan mode. This is to eliminate the possibility of introduction of UVC projected from the UVC LED element into an oral cavity while the handheld scanner scans the inside of the oral cavity. In addition, this is because when UVC is projected from the UVC LED element while the handheld scanner scans the inside of the oral cavity, there is a possibility that the handheld scanner does not obtain precise scan data due to UVC.

In an embodiment, the handheld scanner may control the UVC LED element not to operate while a projector projects light. In an embodiment, the handheld scanner may perform preheating for a preset time before scanning, such that the temperature of the handheld scanner becomes an appropriate operating temperature. In general, when being powered on, the handheld scanner may perform preheating.

In an embodiment, the handheld scanner may control a preheating operation of the handheld scanner through an operating time of the UVC LED element and/or sensing of the temperature inside the handheld scanner accordingly.

For example, when the handheld scanner is powered on and then the UVC LED element operates, the handheld scanner may omit a preheating operation of the handheld scanner or may shorten a preheating time, in consideration of an operating time of the UVC LED element. The handheld scanner may shorten the preheating time or may omit the preheating operation, by sensing an increase in temperature inside the handheld scanner according to the operation of the UVC LED element and comparing the temperature inside the handheld scanner with an appropriate operating temperature. The handheld scanner may perform preheating only when the temperature inside the handheld scanner is lower than an operating temperature suitable for scanning, by checking the temperature inside the handheld scanner periodically or at random time intervals.

In an embodiment, when a user does not use the handheld scanner for a certain period of time after scanning a patient's oral cavity by using the handheld scanner, the handheld scanner may automatically enter the standby mode.

In an embodiment, when the handheld scanner enters the standby mode at a time point of t3, the handheld scanner may recognize the entering into the standby mode as the occurrence of the first event. The handheld scanner may allow the UVC LED element to be turned on at the time point of t3 in response to the occurrence of the first event.

Alternatively, in an embodiment, the handheld scanner may receive a scan mode off command as a control signal from the user input unit or data processing device included in the handheld scanner while performing a scan operation until the time point of t3. When receiving the scan mode off command, the handheld scanner may identify the reception of the scan mode off command as the occurrence of the first event. The handheld scanner may allow the UVC LED element to be turned on at the time point of t3 in response to the occurrence of the first event. In an embodiment, when a time of Δt elapses after the UVC LED element is turned on and the UVC LED element irradiates UVC for Δt, which is a certain amount of preset time, the handheld scanner may identify that UVC is irradiated for Δt after the UVC LED element is turned on as the occurrence of the second event. In other words, the handheld scanner may allow the UVC LED element to be automatically turned off at a time point of t3+Δt.

In an embodiment, calibration of the handheld scanner may be performed. In an embodiment, the handheld scanner may identify, as the occurrence of the first event, a case where the calibration ends. In response to the ending of the calibration, the handheld scanner may allow the UVC LED element to be automatically turned on at a time point of t4, at which the calibration ends, to irradiate UVC for the time of Δt.

In an embodiment, the handheld scanner may allow the UVC LED element to be turned on at a time point of t5 in response to the occurrence of the first event. Afterwards, the handheld scanner may receive a power off command for the handheld scanner from the user input unit or data processing device included in the handheld scanner at a time point of t5+Δt'''. When receiving the power off command for the handheld scanner, the handheld scanner may identify the reception of the power off command as the occurrence of the second event. In response to the occurrence of the second event, the handheld scanner may also allow the UVC LED element to be turned off together with the handheld scanner at a the time point of t5+Δt'''.

Figure 11:
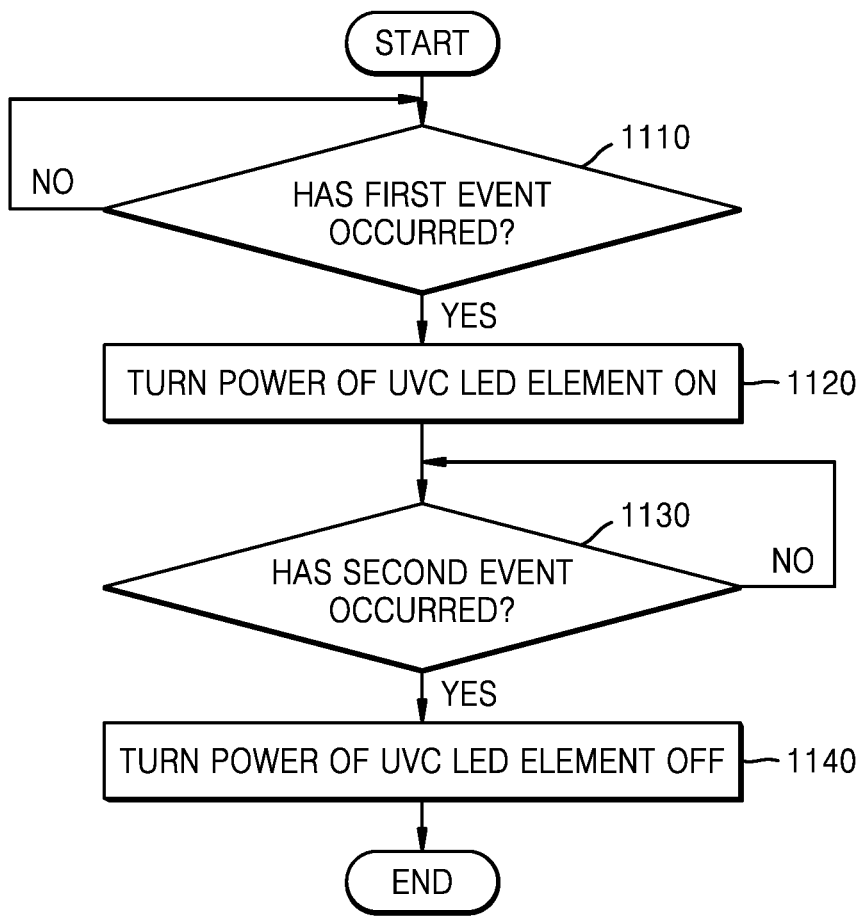
FIG. 11 is a flowchart showing an image processing method according to an embodiment.

FIG. 11 is a flowchart showing an intraoral image processing method according to an embodiment.

Referring to FIG. 11, a handheld scanner may identify whether a first event has occurred (operation 1110). In an embodiment, the first event may include receiving a first control signal including at least one of a power on command for the handheld scanner and a power on command for the UVC LED element. When receiving the first control signal from a data processing device through a user input unit or a communication module, the handheld scanner may identify the reception of the first control signal as the occurrence of the first event.

In addition, in an embodiment, the first event may include at least one of a case where calibration of the handheld scanner ends, a case where the handheld scanner enters a standby mode, and a case where a preset time elapses after the handheld scanner enters the standby mode.

When the first event has occurred, the handheld scanner may allow the UVC LED element to be turned on (operation 1120).

The handheld scanner may identify whether a second event has occurred while the UVC LED element is turned on to irradiate UVC (operation 1130).

In an embodiment, the second event may include receiving a second control signal. The second control signal may include at least one of a scan mode entry command, a power off command for the handheld scanner, and a power off command for the UVC LED element. When receiving the second control signal from the data processing device through the user input unit or the communication module, the handheld scanner may identify the reception of the second control signal as the occurrence of the second event. In addition, in an embodiment, the second event may include the UVC LED element being turned on to irradiate UVC and elapsing of a preset time.

When the second event has occurred, the handheld scanner may allow the UVC LED element to be powered off (operation 1140).

A data processing method according to an embodiment of the present disclosure may be implemented in the form of a program command to be executed through various computer devices and recorded on a computer-readable medium. In addition, the embodiment of the present disclosure may include a computer-readable storage medium having recorded thereon one or more programs including at least one instruction to execute a data processing method.

In addition, the intraoral image processing method according to the embodiment of the present disclosure described above may be implemented as a computer program product including a computer-readable recording medium having recorded thereon a program for implementing an intraoral image processing method performed by an intraoral image processing device, the intraoral image processing method including controlling of one or more UVC LED elements included in a handheld scanner to be turned on in response to detecting a first event, and controlling of the one or more UVC LED elements to be turned off in response to detecting a second event while the one or more UVC LED elements are turned on to operate.

The computer-readable storage medium may include program commands, data files, and data structures either alone or in combination. Examples of the computer-readable storage medium may include magnetic media such as hard disks, floppy disks, or magnetic tapes, optical media such as CD-ROMs or DVDs, and magneto-optical media such as floptical disks, and hardware devices such ROMs, RAMs, or flash memories configured to store and execute program commands.

Here, a machine-readable storage medium may be provided in the form of a non-transitory storage medium. Here, the "non-transitory storage medium" may mean that the storage medium is a tangible device. Also, the "non-transitory storage medium" may include a buffer in which data is temporarily stored.

Although embodiments have been described above in detail, the scope of the present disclosure is not limited thereto and various modifications and improvements made by those of ordinary skill in the art by using the basic concept of the present disclosure defined in the following claims are also included in the scope of the present disclosure.

The invention claimed is:

1. A handheld scanner comprising:
one or more UVC LED elements; and
a processor configured to execute one or more instructions,
wherein the processor is further configured to, by executing the one or more instructions:
control the one or more UVC LED elements to be turned on in response to detecting a first event; and
control the one or more UVC LED elements to be turned off in response to detecting a second event while the one or more UVC LED elements are turned on,
wherein an interior surface of a frame of the handheld scanner and a surface of at least one component inside the frame are made of reflective materials, and
UVC emitted by the one or more UVC LED elements is reflected by the reflective materials into the interior of the frame, sterilizing at least one of the air inside the handheld scanner, the surfaces of the at least one component included within the handheld scanner, and the interior surface of the frame of the handheld scanner.

2. The handheld scanner of claim 1, further comprising:
a user input unit; and
a communicator configured to transmit/receive information to/from a data processing device,
wherein the first event comprises at least one of receiving a first control signal through the user input unit, and receiving a first control signal from the data processing device through the communicator, and
the first control signal comprises at least one of a scan mode off command, a power on command for the handheld scanner, and a power on command for the one or more UVC LED elements.

3. The handheld scanner of claim 1, wherein the first event comprises at least one of ending of calibration of the handheld scanner, entering a standby mode, which is performed by the handheld scanner, and elapsing of a preset time after the handheld scanner enters the standby mode.

4. The handheld scanner of claim 1, further comprising a projector comprising a light source,
wherein the processor is further configured to, by executing the one or more instructions, prevent the light source included in the projector and the one or more UVC LED elements from operating at the same time.

5. The handheld scanner of claim 1, further comprising a camera configured to obtain two-dimensional image data about an object,
wherein the processor is further configured to, by executing the one or more instructions, prevent the camera from obtaining the two-dimensional image data while the one or more UVC LED elements are turned on to operate, or prevent the two-dimensional image data, obtained by the camera while the one or more UVC LED elements are turned on to operate, from being used when a three-dimensional image is generated.

6. The handheld scanner of claim 1, further comprising: a user input unit; and a communicator configured to transmit/receive information to/from a data processing device, wherein the second event comprises at least one of receiving a second control signal through the user input unit, and receiving a second control signal from the data processing device through the communicator, and the second control signal comprises at least one of a scan mode entry command, a power off command for the handheld scanner, and a power off command for the one or more UVC LED elements.

7. The handheld scanner of claim 1, wherein the second event comprises an elapse of a preset time after the one or more UVC LED elements are turned on to irradiate UVC.

8. The handheld scanner of claim 1, wherein the processor is further configured to, by executing one or more instructions, when the one or more UVC LED elements are turned on to operate, perform a scan operation by omitting preheating of the handheld scanner, or perform a scan operation after preheating the handheld scanner for a time shorter than a preset preheating time.

9. The handheld scanner of claim 1, further comprising a fan configured to introduce outside air, wherein the one or more UVC LED elements are arranged in a path where a flow rate of the outside air introduced by the fan is greater than or equal to a reference value.

10. The handheld scanner of claim 1, further comprising an optical module, wherein the one or more UVC LED elements are arranged in the optical module.

11. The handheld scanner of claim 1, further comprising: a handheld scanner main body; and a tip coupled to the handheld scanner main body in a detachable manner, wherein the one or more UVC LED elements are arranged near a portion of the handheld scanner main body, which is coupled to the tip.

12. A data processing device comprising:

a communicator configured to transmit/receive information to/from a handheld scanner including one or more UVC LED elements;

a memory storing one or more instructions; and a processor configured to execute the one or more instructions stored in the memory, wherein the processor is further configured to, by executing the one or more instructions, control the one or more UVC LED elements included in the handheld scanner to be turned on by transmitting a first control signal to the handheld scanner through the communicator, or control the one or more UVC LED elements to be turned off by transmitting a second control signal to the handheld scanner through the communicator while the one or more UVC LED elements are turned on, wherein an interior surface of a frame of the handheld scanner and a surface of at least one component inside the frame are made of reflective materials, and wherein the processor is configured to control the one or more UVC LED elements to turn on, such that UVC emitted by the one or more UVC LED elements is reflected by the reflective materials into the interior of the frame, thereby sterilizing at least one of the air inside the handheld scanner, the surfaces of the at least one component included within the handheld scanner, and the interior surface of the frame of the handheld scanner.

13. The data processing device of claim 12, wherein the first control signal comprises at least one of a scan mode off command, a power on command for the handheld scanner, and a power on command for the one or more UVC LED elements, and the second control signal comprises at least one of a scan mode entry command, a power off command for the handheld scanner, and a power off command for the one or more UVC LED elements.

14. The data processing device of claim 12, further comprising: a user input unit of the data processing device; and a display, wherein a user interface screen for receiving a selection of whether to perform UVC LED element auto-on is output through the display, a selection of the UVC LED element auto-on is received through the user input unit of the data processing device in response to the user interface screen, and the processor is further configured to, by executing the one or more instructions, in response to receiving the selection of the UVC LED element auto-on, control the one or more UVC LED elements mounted in the handheld scanner to be powered on by transmitting the first control signal to the handheld scanner through the communicator, or control the one or more UVC LED elements to be powered off by transmitting the second control signal to the handheld scanner through the communicator.

15. An image processing method performed by an image processing device, the method comprising:

controlling one or more UVC LED elements included in a handheld scanner to be turned on in response to detecting a first event; and controlling the one or more UVC LED elements to be turned off in response to detecting a second event while the one or more UVC LED elements are turned on, wherein an interior surface of a frame of the handheld scanner and a surface of at least one component inside the frame are made of reflective materials, and wherein UVC emitted by the one or more UVC LED elements is reflected by the reflective materials into the interior of the frame, sterilizing at least one of the air inside the handheld scanner, the surfaces of the at least one component included within the handheld scanner, and the interior surface of the frame of the handheld scanner.

16. The method of claim 15, wherein the first event comprises at least one of receiving a first control signal, ending of calibration of the handheld scanner, entering a standby mode, which is performed by the handheld scanner, and elapsing of a preset time after the handheld scanner enters the standby mode, and the first control signal comprises at least one of a scan mode off command, a power on command for the handheld scanner, and a power on command for the one or more UVC LED elements.

17. The method of claim 15, wherein the second event comprises at least one of receiving a second control signal, and elapsing of a preset time after the one or more UVC LED elements irradiate UVC, and the second control signal comprises at least one of a scan mode entry command for the handheld scanner, a power off command for the handheld scanner, and a power off command for the one or more UVC LED elements.

\* \* \* \* \*